United States Patent [19]
Mendoza et al.

[11] Patent Number: 5,994,707
[45] Date of Patent: Nov. 30, 1999

[54] MODULAR FIBER OPTIC FLUOROMETER AND METHOD OF USE THEREOF

[75] Inventors: Edgar A. Mendoza, Redondo Beach; James E. Sorenson, Onyx; Robert A. Lieberman, Torrance; Thomas C. Forrester, Monrovia, all of Calif.

[73] Assignee: Physical Optics Corporation, Torrance, Calif.

[21] Appl. No.: 08/819,050

[22] Filed: Mar. 18, 1997

[51] Int. Cl.$^6$ .................................................. G01N 21/64
[52] U.S. Cl. ..................................... 250/458.1; 250/459.1
[58] Field of Search ............................... 250/458.1, 459.1

[56] References Cited

U.S. PATENT DOCUMENTS

| | | | |
|---|---|---|---|
| 4,840,485 | 6/1989 | Gratton | 356/317 |
| 4,855,930 | 8/1989 | Chao et al. | 364/497 |
| 5,151,869 | 9/1992 | Alcala | 364/497 |
| 5,196,709 | 3/1993 | Berndt et al. | 250/458.1 |
| 5,212,386 | 5/1993 | Gratton et al. | 250/458.1 |
| 5,257,202 | 10/1993 | Feddersen et al. | 364/498 |
| 5,281,825 | 1/1994 | Berndt et al. | 250/458.1 |
| 5,317,162 | 5/1994 | Pinsky et al. | 250/461.2 |
| 5,323,008 | 6/1994 | Studholme et al. | 250/458.1 |
| 5,323,010 | 6/1994 | Gratton et al. | 250/458.1 |
| 5,548,124 | 8/1996 | Takeshima et al. | 250/458.1 |

FOREIGN PATENT DOCUMENTS

WO87/06698  11/1987  WIPO ................................. 250/458.1

OTHER PUBLICATIONS

D. J. S. Birch, R. E. Imhof, and A. Dutch, "Pulse fluorometry using simultaneous acquisition of fluorescence and excitation." *Rev. Sci. Instrum.* vol. 55, No. 8, pp. 1255–1264, Aug. 1984.

*Primary Examiner*—Constantine Hannaher
*Attorney, Agent, or Firm*—Nilles & Nilles, S.C.

[57] ABSTRACT

A low cost portable fiber optic fluorometer is packaged as a personal computer peripheral and is based on interchangeable modules. One embodiment of the fluorometer comprises an excitation source, a detector, a signal processor, frequency source, wavelength selector, and an optical interface. The optical interface is exclusively fiber optic-based, thereby simplifying optical alignment and reducing the cost of the fluorometer. In another embodiment, the excitation source is an inexpensive monochromatic excitation source. In this case, the monochromatic excitation source and the first wavelength selector are preferably removable and replaceable, so that the fluorometer is advantageously able to generate different excitation wavelengths and detect different emission wavelengths. A fluorescence measurement method comprises the steps of generating an excitation signal; transmitting the excitation signal to a system under study which, in response, generates an emission signal; and detecting both the excitation signal and the emission signal with the fluorometer, and then using the detected excitation signal as a reference signal to calibrate the fluorometer and to nullify distortion errors in the emission signal. The use of the excitation signal as a reference signal provides an advantageously simple way to calibrate the fluorometer and to nullify distortion errors in the emission signal. An alternative method allows the precise shapes of the emission signal and the excitation signal to be profiled. The fluorometry method and apparatus can both advantageously be used for performing both direct fluorescence lifetime measurements and for performing phase fluorometry.

21 Claims, 20 Drawing Sheets

$$T_{TOTAL} = T_{T1} + T_{T2}$$
$$= T_{T1} + (T_P - (T_F - T_A))$$

MODULAR FIBER OPTIC FLUOROMETER AND METHOD OF USE THEREOF

BACKGROUND OF THE INVENTION

1 Field of the Invention

The present invention relates generally to the field of fluorescence spectroscopy. More particularly, the present invention relates to a low cost portable fiber optic fluorometer that is packaged as a personal computer peripheral or on a personal computer expansion card and is based on interchangeable modules.

2. Discussion of the Related Art

Historically, fluorescence spectroscopy has been widely used in chemical, biochemical, and biomedical research. Although there are a virtually unlimited number of different ways in which fluorescence spectroscopy could be applied, specific fluorescence spectroscopy applications include chemical sensors, process control systems, systems for studying cellular phenomena, systems for determining molecular structure, and temperature and viscosity measurement systems.

A number of different fluorescence spectroscopy techniques exist, including intensity-based techniques and fluorescence lifetime techniques. According to intensity-based techniques, information regarding a system under study is obtained by measuring the relative intensity of emissions from a sample at one or more wavelengths. According to fluorescence lifetime techniques, information is obtained by exciting a fluorescent sample with an excitation signal in the form of a pulse of light, and then directly measuring the exponential decay of the resulting emission signal from the sample. A variation of the fluorescence lifetime technique is phase fluorometry. According to phase fluorometry, information is obtained by illuminating a fluorescent sample with a modulated excitation signal, thereby causing the sample to emit an emission signal which is also modulated. The time delay between excitation of the sample and emission causes a phase difference between the excitation and emission signals. The phase difference is a function of the fluorescence lifetime; accordingly, measuring the phase difference enables the fluorescence lifetime of the system under study to be calculated. Thus, in contrast to the fluorescence lifetime techniques which measure a fluorescence lifetime directly, phase fluorometry involves measuring a fluorescence lifetime indirectly by measuring the phase difference between an excitation signal and an emission signal.

The main advantage of fluorescence spectroscopy is the high sensitivity which can be achieved due to the favorable time scale of fluorescence emissions. Nevertheless, despite this advantage, fluorescence spectroscopy has failed to achieve widespread commercial acceptance outside the laboratory research setting.

The lack of widespread commercial acceptance is due to the fact that existing fluorometers are bulky, expensive, require precise optical alignment, and are difficult to calibrate. Specifically, existing fluorometers comprise numerous large and expensive components. The excitation source is typically a laboratory grade light source, such as a gas laser or a high-powered arc lamp. The detector is typically a spectrograph which collects and records the entire spectrum of light returned from the system under study. (Existing fluorometers are designed to permit the study of fluorescence emission at a wide range of wavelengths, e.g., from the ultraviolet to the near infrared.) Moreover, because precise optical alignment is required between the various subcomponents, existing fluorometers require an optical bench which floats on a pneumatic system in order to reduce vibrations. Finally, calibration of existing fluorometers is extremely difficult, especially in a commercial setting where environmental conditions are more likely to be adverse as compared to a laboratory setting. Existing fluorometers are thus not only expensive to purchase but also are expensive to set up and maintain.

Thus, what is needed is a fluorometer that is relatively inexpensive, that is small in size, that is tolerant to environmental hazards such as vibration, and/or that is relatively easy to calibrate.

SUMMARY AND OBJECTS OF THE INVENTION

A low cost portable fiber optic fluorometer that is packaged as a personal computer peripheral or on a personal computer expansion card and is based on interchangeable modules is disclosed.

A wavelength specific fluorometer comprises a frequency generator, a first monochromatic excitation source, a first wavelength selector, and a detector. The first monochromatic excitation source is coupled to the frequency generator and is adapted for generating a first excitation signal having a first excitation wavelength. The first wavelength selector is adapted for selecting a first emission signal having a first emission wavelength. Advantageously, the use of a monochromatic excitation source drastically reduces the cost of the fluorometer.

In an improvement, the first monochromatic excitation source and the first wavelength selector are removable and replaceable with a second monochromatic excitation source and/or a second wavelength selector, which are respectively adapted for generating a second excitation signal having a second excitation wavelength and for selecting a second emission signal having a second emission wavelength. Thus, the fluorometer is advantageously able to generate different excitation wavelengths and detect different emission wavelengths by removing and replacing the monochromatic excitation source and the wavelength selector.

In another improvement, an exclusively fiber optic interface is used between the fluorometer and the system under study. Advantageously, the use of an exclusively fiber optic interface drastically reduces the cost of the fluorometer, because optical alignment is simplified and because the fluorometer is more tolerant to vibrations.

Other objects, features, and advantages of the present invention will become apparent to those skilled in the art from the following detailed description and accompanying drawings. It should be understood, however, that the detailed description and specific examples, while indicating preferred embodiments of the present invention, are given by way of illustration and not limitation. Many modifications and changes within the scope of the present invention may be made without departing from the spirit thereof, and the invention includes all such modifications.

DESCRIPTION OF PREFERRED EMBODIMENTS

Figure 1A:
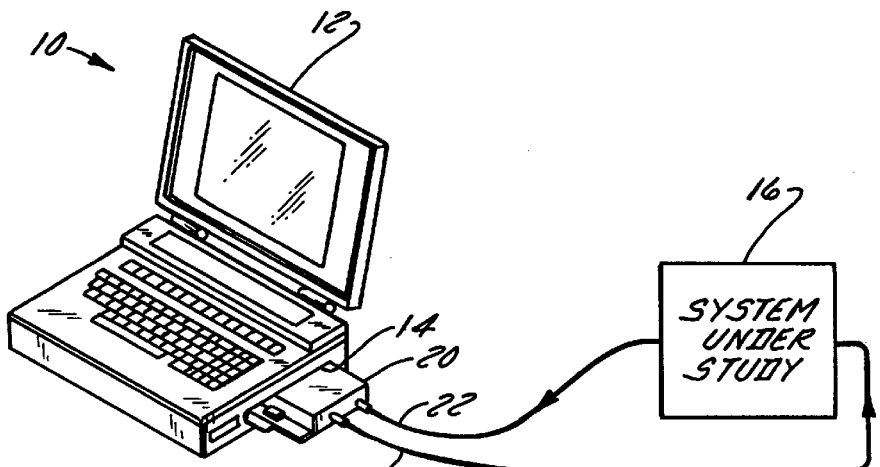
FIG. 1A illustrates a perspective view of a laptop modular fluorometer system according to the present invention.
Figure 1B:
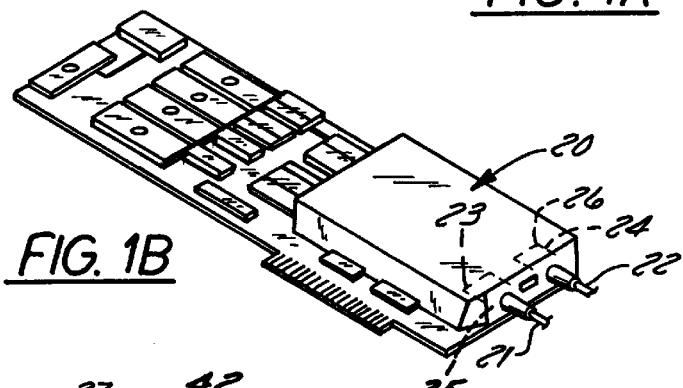
FIG. 1B illustrates a perspective view of a modular fluorometer packaged on a laptop computer expansion card according to the present invention.

Referring to FIGS. 1A–1B, the general structural features of a modular fluorometer system 10 according to the present invention are illustrated. The modular fluorometer system 10 comprises a laptop computer 12, a modular fluorometer 20 which is removably plugged into a bay 14 of the laptop computer 12, and a system under study 16. It will be appreciated that the system under study 16 could be any type of system wherein fluorometric measurements may be made.

The modular fluorometer 20 includes an optical output 21 and an optical input 22. The optical output 21 is driven by a light source 25 coupled to a frequency module 23, and provides an excitation signal to the system under study 16. The excitation signal excites a sample in the system 16 to produce an emission signal. The emission signal as well as the excitation signal return to the modular fluorometer 20 through optical input 22. (As detailed below, the excitation signal is returned to the fluorometer 20 in order to form a reference signal against which the emission signal may be compared, thereby greatly simplifying calibration and nullification of distortion.) The optical input 22 receives two separate optical fibers, i.e., one for the excitation signal and one for the emission signal. After being received at the optical input 22, the emission and excitation signals are filtered by a filter set 24 and selectively detected by a detector 26.

It should thus be apparent that the interface between the electronics of the fluorometer 20 and the system under study 16 is an exclusively fiber optic interface. Advantageously, the all-fiber format drastically reduces the cost of the fluorometer 20. Since the light always stays in the fibers, there is no need to precisely align a plurality of large subcomponents as in a non-exclusively fiber optic system. The fluorometer 20 is thus easier to set up and maintain. Moreover, the fluorometer 20 is more tolerant to vibrations, and there is no need for an optical bench which floats on a pneumatic system to reduce vibrations. Also, the need for an expensive sample chamber is eliminated.

In one preferred embodiment, one or more of the frequency module 23, the light source 25, the filter set 24 and the detector 26, are removable, modular, single-frequency solid-state components. Advantageously, the use of single-frequency, solid-state components also drastically reduces the cost of the fluorometer 20. For example, rather than using an expensive gas laser, a solid-state laser diode (LD) or light emitting diode (LED) is used. Further, rather than using an expensive spectrograph which is designed to collect and record the entire spectrum of light returned from the system under study, an inexpensive single-frequency detector 26 is used to detect an emission signal having a wavelength generally equal to the wavelength of an emission signal selected by a wavelength selector.

Assuming all are modular, the frequency module 23, the light source 25, the filter set 24 and the detector 26 are connected to the fluorometer 20 by way of connectors which permit them to be removed and replaced. Thus, these components may be replaced with components which operate at a different single frequency, limited range of frequencies, or wide range of frequencies. Therefore, to a large extent, the flexibility of more expensive systems is still achieved.

Figure 1C:
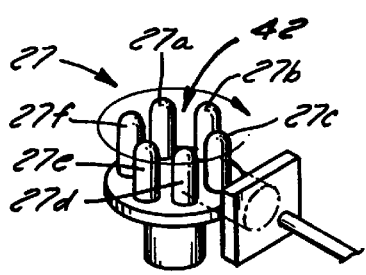
FIG. 1C illustrates a perspective view of components from an alternative removable modular excitation light source according to the present invention.

FIG. 1C illustrates an alternative light source 27 which comprises a plurality of radiation sources 27a–27f which may cover the range, e.g., from 400 nm to 900 nm. The plurality of radiation sources are provided in the form of an LED RAINBOW turret assembly. The spectrum of light that can be produced by the modular light source 27 can be discretely varied within set ranges by simply rotating the turret assembly, assuming each of the plurality of radiation sources 42 emits energy within a different subspectrum. Alternatively, two or more of the plurality of radiation sources 42 can be selected to emit energy within the same (or overlapping) spectral ranges so as to provide redundancy and a quick replacement mechanism, so that a spent radiation source can be replaced merely by rotating the turret assembly.

Figure 1D:
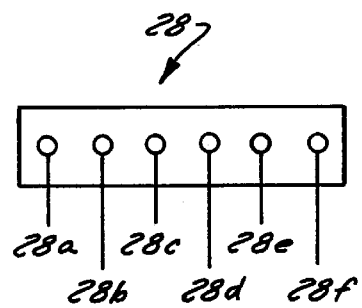
FIG. 1D illustrates a linear array light source which forms another alternative removable modular excitation light source according to the present invention.

FIG. 1D illustrates a second alternative light source 28. The light source 28 is a linear array light source comprising a plurality of radiation sources 28a–28f. The particular radiation source 28a–28f used can be selected, e.g., by way of an optical switch. The idea of the light source 28 is the same as that of light source 27, i.e., to permit the spectrum of light that can be produced to be discretely varied within set ranges simply by selecting a different radiation source. In this case, however, the light source 28 does not rotate, thereby avoiding the use of moving parts.

Figure 2:
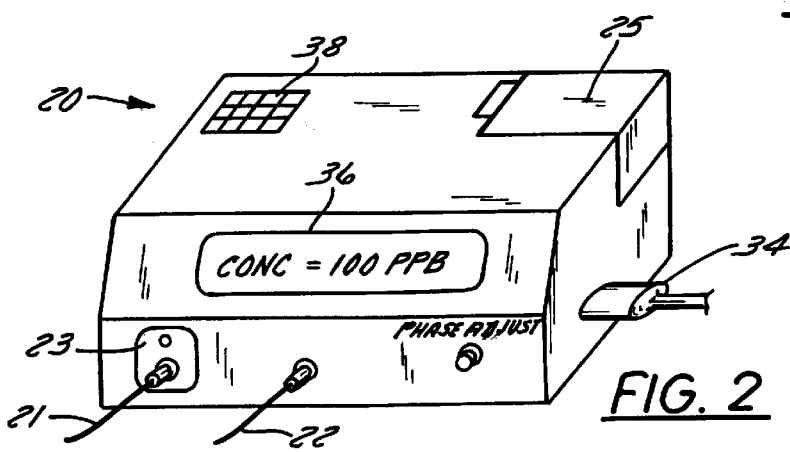
FIG. 2 illustrates a perspective view of an alternative packaging configuration for a fluorometer according to the present invention.

FIG. 2 illustrates a perspective view of an alternative packaging configuration for the fluorometer according to the present invention. In this case, rather than being packaged on an expansion card, the fluorometer 20 is packaged as a stand-alone peripheral for the computer 12, and is connected to the computer 12 by way of an RS-232 connection 34. Further, the fluorometer 20 may also be provided with a display 36 and keypad 38, along with additional processing capabilities, in order to make continuous connection with the computer 12 optional.

Figure 3A:
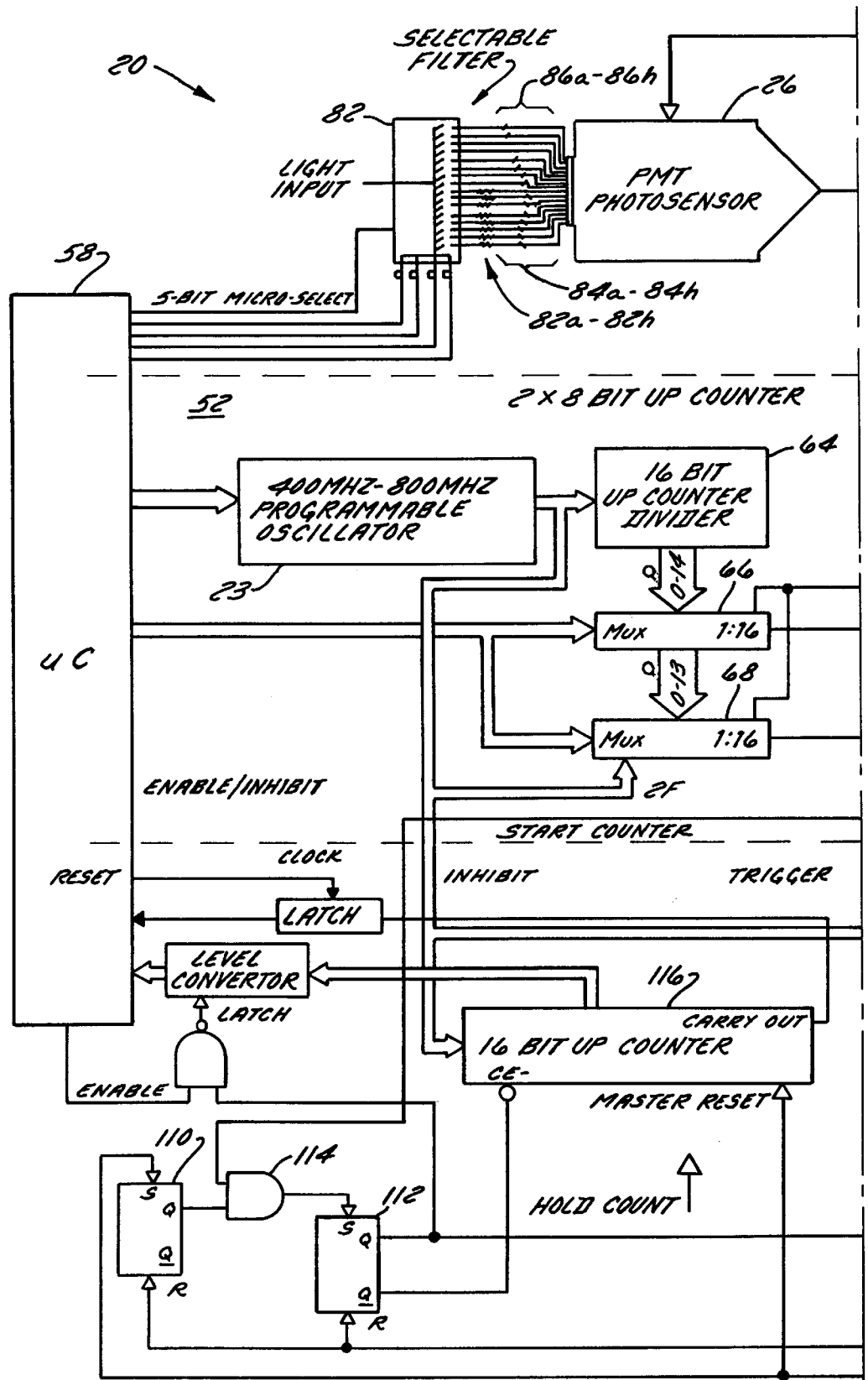
FIGS. 3A–3C illustrate a schematic circuit diagram of a fluorometer according to the present invention.
Figure 3B:
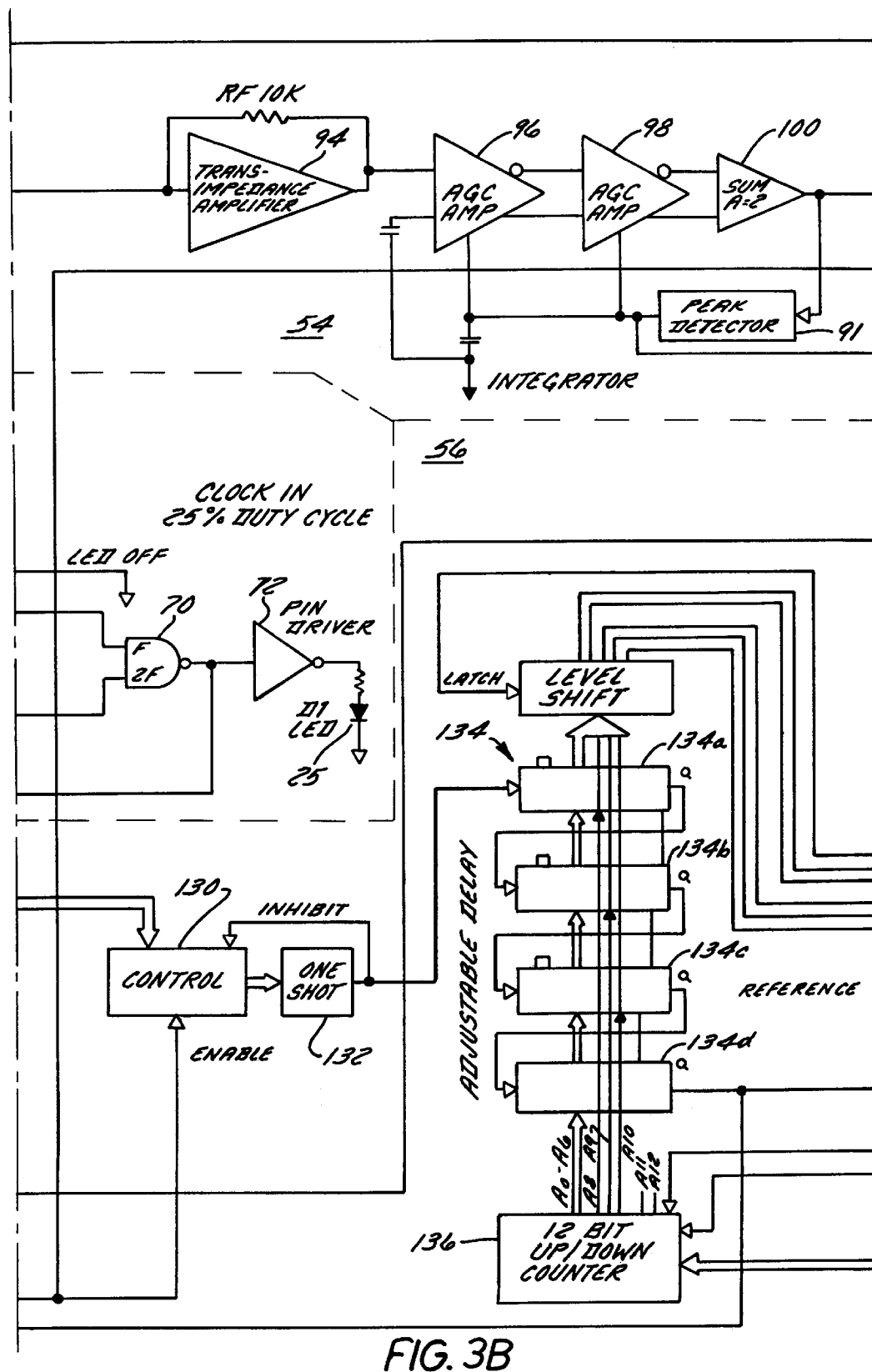
Figure 3C:
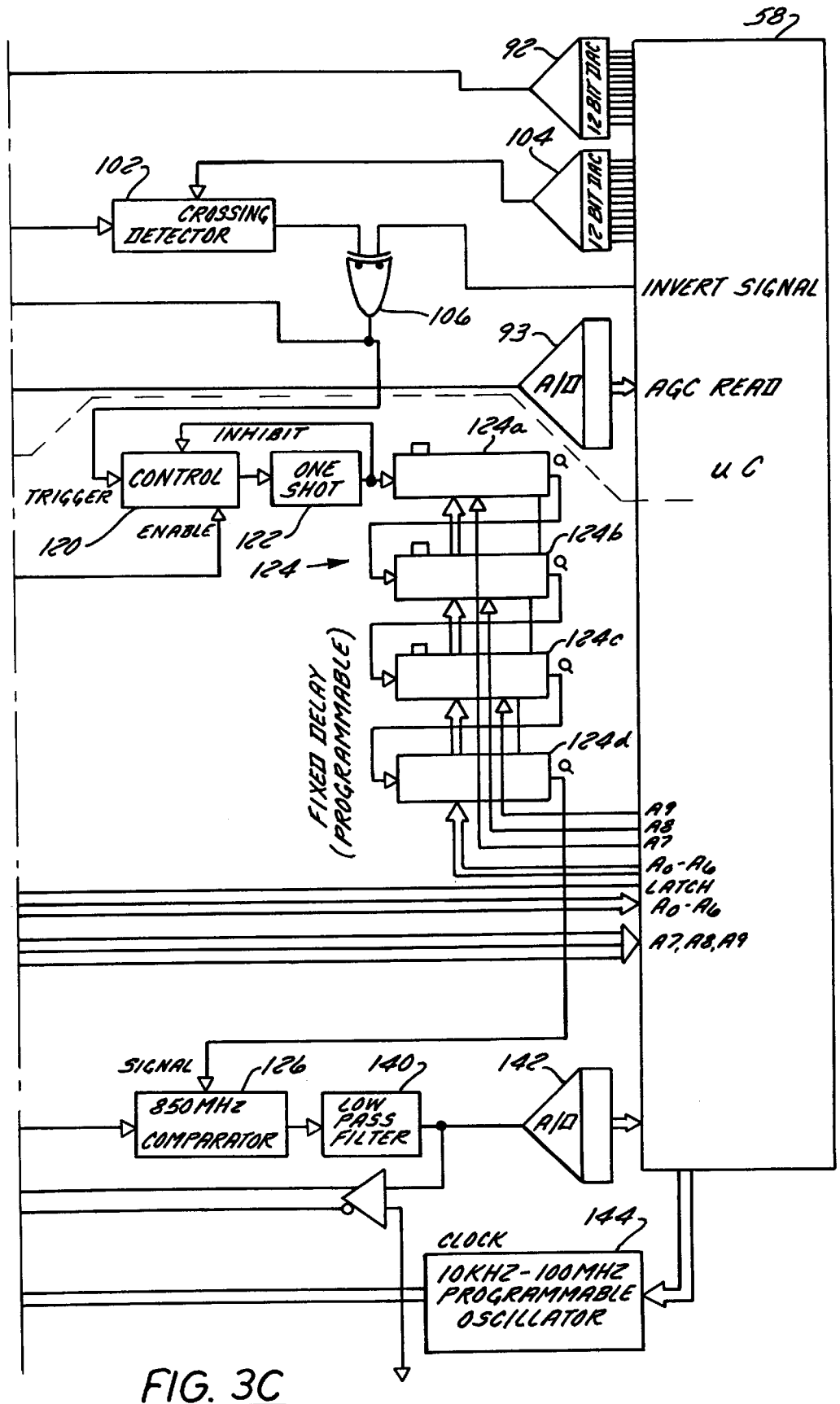

FIGS. 3A–3C illustrates a schematic circuit diagram of a fluorometer circuit which could be used by the fluorometer 20. The fluorometer circuit comprises three major subcircuits including a source subcircuit 52, a detection subcircuit 54, and a signal processing subcircuit 56. The subcircuits 52–56 share processing capabilities which, for purposes of illustration, are illustrated in the form of a single microprocessor 58 (which is illustrated on both sides of the drawing). In practice, however, the microprocessor 58 could be formed of two or more different microprocessors.

The source subcircuit 52 is responsible for generating an excitation signal. For this purpose, the source subcircuit 52 comprises the source module 25 (illustrated as an LED) and the frequency module 23 as previously described. The source subcircuit 52 also comprises a sixteen bit up counter/frequency divider 64, 1:16 multiplexers 66 and 68, NAND gate 70 and driver 72. The purpose of this additional circuitry is to reduce the frequency of the signal generated by the frequency module 23, to add more programmability to the frequency module 23, and to condition the low level signal generated by the frequency module 23 and remaining components so as to make it adequate for driving the LED 25.

More specifically, the frequency module 23 in the embodiment illustrated in FIGS. 3A–3C is a programmable oscillator which outputs a clock signal having a frequency 2F. The frequency 2F of the signal generated by the frequency module 23 is in the 400 MHz to 800 MHz range, and is chosen by the microprocessor 58.

The clock signal is received by the up counter/frequency divider 64 which has sixteen output bits 0–15. The frequency of each $n^{th}$ output bit is $\frac{1}{2}^{n+1}$ the frequency of the clock signal. Thus, the $Q_0$ bit has a frequency which is equal to $\frac{1}{2}*2F=F$, whereas the $Q_{15}$ bit has a frequency which is equal to $1/65536*2F=F/32768$.

The $Q_0$–$Q_{14}$ bits of the up counter 64 are input to fifteen of the sixteen inputs of the 1:16 multiplexer 66. (Note that the most significant bit weight input of the multiplexer 66 is connected to ground. As a result, when this input bit is selected, the LED 25 turns off.) By changing the select inputs (not illustrated) of the multiplexer 66, one of the $Q_0$–$Q_{14}$ inputs bits can be chosen as an output bit. Thus, by changing the select inputs of the multiplexer 66, the multiplexer output frequency can be chosen so as to correspond to the frequency of one of the bits $Q_0$–$Q_{14}$. The frequency of the multiplexer 66 output thus ranges from F to F/16384, depending on the setting of the select inputs of the multiplexer 66.

The $Q_0$–$Q_{13}$ bits of the up counter 64 are also input to fourteen of the sixteen inputs of the 1:16 multiplexer 68. In this case, the least significant bit weight input of the multiplexer 68 is driven directly by the programmable oscillator 23. The next fourteen bits are driven by the $Q_0$–$Q_{13}$ output bits of the up counter 64, and the last bit is again connected to ground to enable the LED to be turned off. The select inputs of the multiplexer 68 are coupled to the select inputs of the multiplexer 66. Thus, the frequency of the multiplexer 68 output ranges from 2F to F/8192, depending on the setting of the select inputs of the multiplexer 66. Notably, the output frequency of the multiplexer 68 is always exactly twice that of the multiplexer 66, and corresponds to the frequency of either the programmable oscillator 23 or one of the $Q_0$–$Q_{13}$ output bits.

Figure 4:
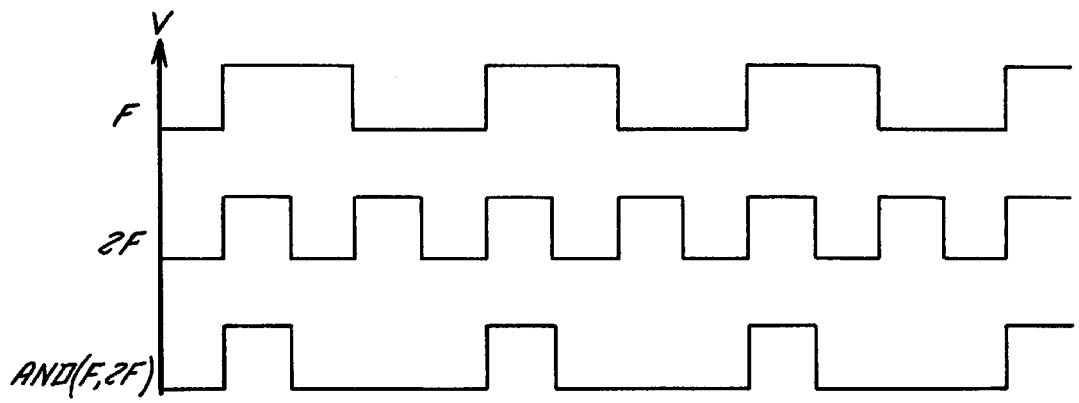
FIG. 4 illustrates the generation of an excitation signal having a twenty-five percent duty cycle in the fluorometer circuit illustrated in FIGS. 3A–3C, according to the present invention.

The outputs of the multiplexers 66 and 68 are received by a NAND gate 70, whose output is inverted by a pin driver 72. As can be seen in FIG. 4, the output of the pin driver 72 (which is an "AND" of the multiplexer outputs) is a signal having a frequency F and a 25% duty cycle. (Advantageously, the use of a 25% duty cycle enhances the peak drive capability of the LED 25.) The driver 72 conditions the low level signal generated by the frequency module 23 and remaining components so as to make it adequate for driving the LED 25. The output of the driver 72 is then received by the LED 25.

As previously described with respect to FIGS. 1A–1B, the LED 25 is coupled to the optical output 21 of the fluorometer 20. The optical output 21 thus outputs the excitation signal generated by the LED 25 to an optical fiber, which transmits the excitation signal to the system under study 16. The emission and excitation signals are then returned to the optical input 22 via optical fibers.

The second major subcircuit is the detection subcircuit 54, which receives the emission and excitation signals from the system under study 16 by way of the optical input 22. The purpose of the detection subcircuit 54 is to detect the incoming excitation and emission signals, to select between them so that the signal processing subcircuit 56 can process one signal at a time, and to generate a signal which indicates when the excitation/emission signal crosses a threshold.

More specifically, the emission and excitation signals are returned to the optical input 22 via optical fibers and are received at an optical switch 82. In its simplest form, the optical switch 82 is a single pole, double throw optical switch. The optical switch 82 is used to alternately route light between two filters (which together form the removable modular filter set 24 discussed above), i.e., one filter which filters out the excitation signal and one filter which filters out the emission signal. As a result, the optical switch 82 switches between the emission signal and the excitation signal, enabling the detector 26 and the signal processing subcircuit 56 to examine one signal at a time.

In the illustrated embodiment, the optical switch 82 is formed of a 1×16 optical fiber switch. The optical switch may be used in a multi-wavelength system, e.g., where the source module comprises eight LED's which each operate at a different wavelength. In this case, when the signal processing subcircuit 56 is examining the excitation signal, one of a plurality of filters 84a–84h are used to filter out the emission signal which could be one of a plurality of different possible wavelengths, depending on the wavelength of the excitation signal. Similarly, when the signal processing subcircuit 56 is examining the emission signal, one of a plurality of filters 86a–86h are used to filter out the excitation signal, which could be one of a plurality of different possible wavelengths, depending on the particular LED used. Preferably, a plurality of attenuators 82a–82h are also used for attenuating the excitation signal, which would otherwise have a signal strength which is substantially larger than that of the emission signal.

The output of the optical switch 82 is received by the detector 26, which in the embodiment of FIGS. 3A–3C is a photomultiplier tube. The detector 23 could also, for example, be an avalanche photodetector or a PIN photodiode. The photomultiplier tube has an adjustable gain which is controlled by the microprocessor 58 in conjunction with the digital-analog converter 92. The gain of the photomultiplier tube 26 is controlled so as to avoid clipping and so as to output a signal to the automatic gain control amplifier 96 which has acceptable dynamic characteristics. The gain of the photomultiplier tube 26 is controlled by the microprocessor 58 based on input signals received from the peak detector 91 by way of the analog-digital convertor 93.

The output of the photomultiplier tube 26 is an output current. This output current is converted to an output voltage by the transimpedance amplifier 94. The output voltage is then received by automatic gain control circuitry formed of automatic gain control amplifiers 96 and 98 and summing amplifier 100, which causes the peaks and the slopes of pulses of the emission and excitation signals to be held at constant levels. The automatic gain control amplifiers are controlled based on a feedback control signal provided by the peak detector 91.

The output of the automatic gain control circuitry is received by the programmable crossing detector 102. The crossing detector 102 is similar to a zero crossing detector except that it is programmable, so that it can detect other (non-zero) crossings in addition to zero crossings. The programmable crossing detector 102 is programmed by the microprocessor 58 using the digital-analog converter 104. An XOR gate 106 enables the signal to be inverted so that either falling or rising edges can be used.

The third major subcircuit is the signal processing subcircuit 56, which receives the output signal from the XOR gate 106. The purpose of the signal processing circuit is to generate timing information based on the crossing information received from the crossing detector 102. The timing information may be, for example, the amount of time between when the LED 25 was initially triggered until the point in time at which the emission signal decays to a particular signal level (i.e. the level set by the crossing detector 102). As discussed further below, multiple measurements may then be made of both the excitation signal and the emission signal in order to measure the fluorescence lifetime or to profile the fluorescence decay.

The signal processing subcircuit 56 has two modes of operation. In a first mode of operation, coarse time measurements are made using only a coarse sixteen bit up counter 116. The coarse counter 116 is driven by the programmable oscillator 23, and has a resolution which is equal to the period of the programmable oscillator 23. In other words, if the programmable oscillator is programmed to oscillate at 400 MHz (and therefore has a period $T_P$=2.5 ns), the resolution of the coarse counter 116 is 2.5 ns.

In a second mode of operation, fine time measurements are made using the coarse counter 116 in combination with delay circuits 124 and 134. The delay circuits 124 and 136 permit the user to make measurements which have a resolution that is higher than that defined by the resolution of the coarse counter 116.

Figure 5:
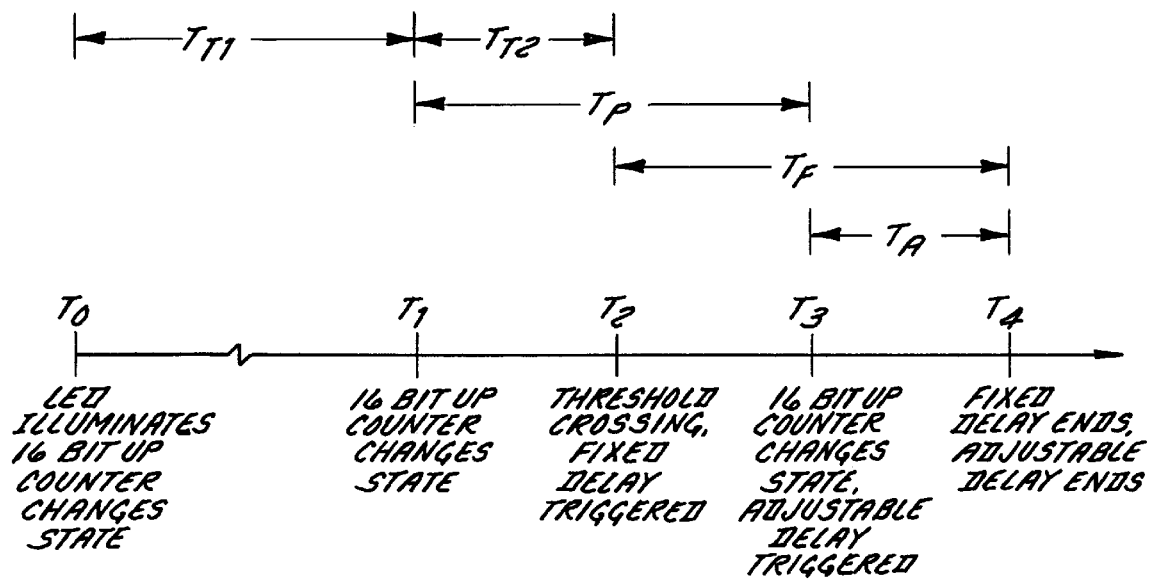
FIG. 5 illustrates a timing sequence relevant to the operation of a signal processing subcircuit in the fluorometer circuit illustrated in FIGS. 3A–3C, according to the present invention.

The overall approach taken during the second mode of operation is best understood with reference to FIG. 5. As illustrated in FIG. 5, the LED initially illuminates at instant $T_0$. The excitation signal propagates to the system under study 16, and then the excitation and emission signals return through optical input 22. The instant $T_1$ is the instant at which the coarse counter 116 undergoes its last state change before the crossing of interest is detected by the crossing detector 102 at an instant $T_2$. When the crossing is detected at the instant $T_2$, a fixed delay having a duration $T_F$ is triggered. Subsequently, the coarse counter 116 changes state again at an instant $T_3$, at which time an adjustable delay having a duration $T_A$ is triggered. The adjustable delay 134 is adjusted such that it terminates at the same time instant $T_4$ as the fixed delay 124.

The fact that the delays 124 and 134 terminate at the same time makes it possible to determine when the crossing occurred relative to the last state change of the coarse counter 116. Thus, it is possible to calculate, based on known parameters, the total elapsed time $T_{TOTAL}$ between the instant at which the LED 25 was initially illuminated and the instant at which the crossing occurred, as illustrated.

Referring again to FIGS. 3A–3C, the operation of the signal processing subcircuit is now discussed in greater detail. The output signal from the XOR gate 106 of the detection subcircuit 54 is received by RS flip flops 110 and 112. It may be noted that the SET input flip flop 112 is coupled to the NAND gate 70 by way of AND gate 114, and is set when the LED 25 is triggered. It may further be noted that the output of the flip flop 112 is coupled to the clear/enable input of the coarse counter 116. Consequently, the coarse counter 116 starts counting when the LED is initially triggered and stops counting when the crossing is detected by the detector 102 (i.e., when the output signal from the XOR gate is received at the RESET inputs of the flip flops 110 and 114).

If all that is required is a coarse time measurement (i.e., the first mode of operation), then no further processing is required. The output bits of the coarse counter 116 are read by the microprocessor 58 and the time measurement is complete.

If a higher resolution time measurement is required (i.e., the second mode of operation) then further processing (including additional crossing detections) is required. In this case, when the crossing is detected, the output signal from the XOR gate 106 causes a control circuit 120 and a one shot generator 122 to generate a first short (one shot) pulse which then propagates through the fixed delay circuit 124. The output of the fixed delay 124 is coupled to a first input of a phase comparator 126.

The fixed delay circuit 124 comprises a plurality of individual delays 124a–124d. The individual delays 124a–124d each have about a 2.5 ns delay capacity. However, the length of each delay is programmable by changing the values of the $A_0$–$A_9$ inputs to the delays 124a–124d with the microprocessor 58. The bit weight of the delays 124a–124d is about 20 ps, and the delays 124a–124d can thus be programmed in 20 ps increments. Nevertheless, despite the fact that the delays 124a–124d can be programmed, they are considered to be fixed since they are programmed first, and the adjustable delays 134a–134d are programmed thereafter. (Note that the fixed delay 124 compensates for the fixed delays in the fluorometer system, whereas the adjustable delay compensates for the delay between the state change of the coarse counter 116 and the detection of a crossing.)

The output signal from the XOR gate 106 also causes a control circuit 130 and a one shot generator 132 to generate a second short (one shot) pulse which then propagates through the adjustable delay circuit 134. The output of the adjustable delay 134 is coupled to the other input of the phase comparator 126.

The adjustable delay circuit 134 comprises a plurality of individual delays 134a–134d. The adjustable delay 134 is similar to the fixed delay in that it is programmable in 20 ps increments. In the case of the adjustable delay circuit 134, however, programming is achieved by way of the twelve bit up counter 136, which changes the values of the $A_0$–$A_{10}$ inputs to the delays 134a–134d. The up counter 136 is driven by the output of the phase comparator 126, which is passed through a low pass filter 140.

Thus, in operation, an initial crossing is detected by the crossing detector 102. Immediately thereafter, the control circuit 120 and one shot generator 122 cause a first one shot pulse to begin propagating through the fixed delay 124. Subsequently, upon the next state change of the coarse counter 116, the control circuit 130 and one shot generator 132 cause a second one shot pulse to begin propagating through the adjustable delay 134. Eventually, the one shot pulses finish propagating through the fixed delay 124 and the adjustable delay 134. At this time, the comparator 126 generates an error signal which is indicative of the time difference between when (1) the first one shot pulse finished propagating through the fixed delay 124 and (2) the second one shot pulse finished propagating through the adjustable delay 134. The error signal drives the up counter 136, so that the length of the adjustable delay 134 is dynamically adjusted responsive to the error signal.

Then, another iteration of the above-described process occurs. In other words, another crossing is detected by the crossing detector 102, then two more one shot pulses propagate through the fixed and adjustable delays 124 and 134, and then another error signal is generated. With each iteration of the process, the time difference between the events (1) and (2) described above decreases, and the error signal is eventually driven to a steady state (or approximately steady state) zero value. Thus, there is an instant $T_4$ (see FIG. 5) at which both the fixed delay 124 and the adjustable delay 134 simultaneously terminate. Accordingly, it is then possible to calculate, with 20 ps resolution, the total elapsed time $T_{TOTAL}$ between the instant at which the LED 25 initially illuminates and the instant at which the crossing occurs.

It should be noted that the programmable oscillator 144 controls the rate at which the up/down counter 136 changes state. Adjusting the oscillation frequency of the oscillator 144 is analogous to adjusting the feedback constant in a feedback control system: If the oscillation frequency is set too high, adjustments are made too rapidly and the error signal tends to fluctuate unacceptably. If the oscillation frequency is set too low, adjustments are made too slowly and it takes an undesirably long amount of time for the error signal to be driven to a steady state (or approximately steady state) zero value.

The error signal is continuously monitored by the microprocessor 58 via the analog-digital converter 142. When the microprocessor 58 detects that the error signal has been driven to an (approximate) steady state zero value, it reads the input bits $A_0$–$A_{10}$ of the adjustable delay 134. Referring again to FIG. 5, the microprocessor 58 is able to calculate the duration $T_A$ of the adjustable delay 134 based on the bits $A_0$–$A_{10}$. Further, based on the input bits $A_0$–$A_9$ of the fixed delay 124, the microprocessor 58 is able to calculate the duration $T_F$ of the fixed delay 124. Additionally, since the frequency of the programmable oscillator 23 is programmed by the microprocessor 58 and is thus known by the microprocessor 58, the period $T_P$ is known to the microprocessor 58. Finally, the microprocessor 58 is able to read the output bits of the coarse counter 116 and is able to calculate the duration $T_{T1}$. The microprocessor 58 thus has all the information it needs to calculate, with 20 ps resolution, the total elapsed time $T_{TOTAL}$ between the instant at which the LED 25 was initially illuminated and the instant at which the crossing occurred.

Figure 6:
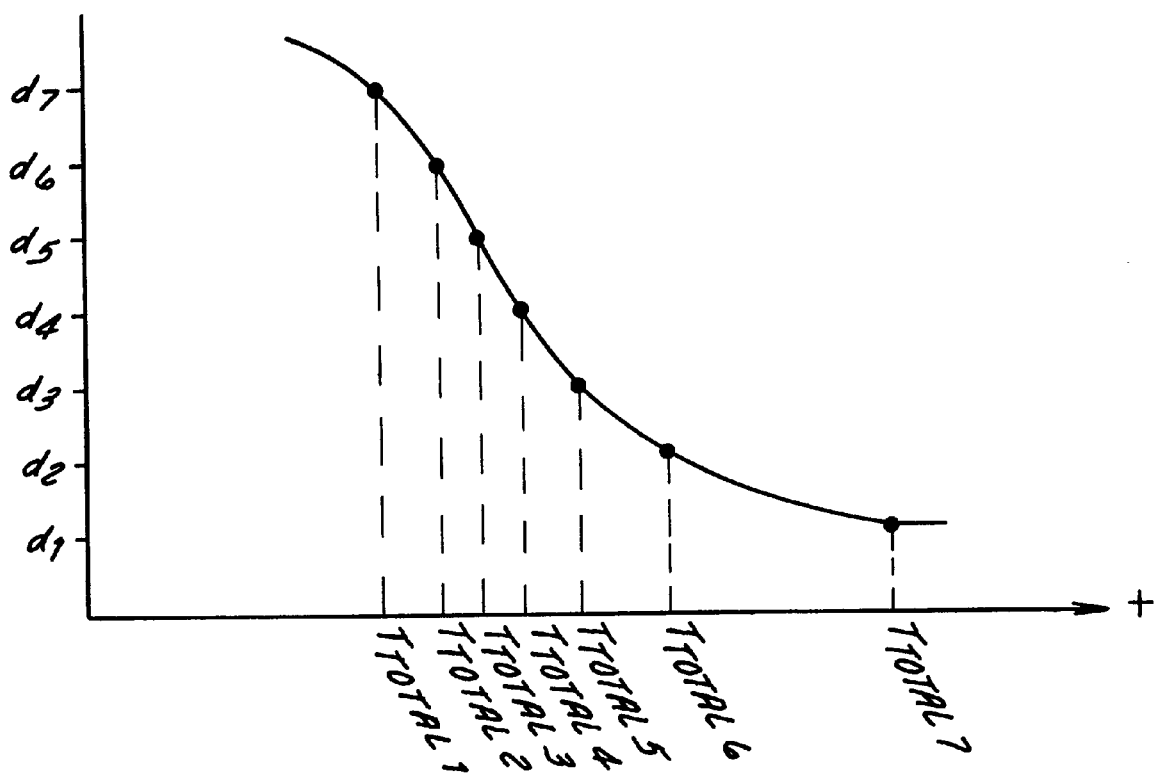
FIG. 6 illustrates pulse profiling achieved by the fluorometer circuit illustrated in FIGS. 3A–3C, according to the present invention.

By varying the programmed level of the crossing detector, a series of different data points may be obtained. Thus, by setting the crossing detector 102 to a plurality of levels $d_1$–$d_7$, it is possible to obtain a profile of a signal which is detected by the detection subcircuit 54, as illustrated in FIG. 6. (In practice, the number of data points taken is much higher than the seven data points illustrated in FIG. 6.) Further, by varying the setting of the optical switch, it is possible to switch back and forth between the excitation signal and the emission signal, and profile both signals. In this manner, it is possible to use the fluorometer illustrated in FIGS. 3A–3C to perform both direct fluorescence life time measurements and to perform phase fluorometry.

Finally, by varying the setting of the programmable oscillator 23, it is possible to sweep a range of frequencies and, e.g., perform pulse profiling at the range of frequencies.

Referring now to FIGS. 7A–7F and FIGS. 8A–8F, the overall operation of the microprocessor 58 to perform a direct lifetime measurement is illustrated. It should be noted that, in the embodiment described in FIGS. 7A–7F and FIGS. 8A–8F, the microprocessor 58 comprises two separate microprocessors which operate concurrently, i.e., a primary microprocessor (FIGS. 7A–7F) and a secondary microprocessor (FIGS. 8A–8F). It should also be noted that there is not a one-to-one correspondence between the two "halves" of the microprocessor 58 illustrated in FIGS. 3A–3C and the primary and secondary microprocessors discussed in FIGS. 7A–7F and FIGS. 8A–8F. The functions performed by the primary and secondary microprocessors are distributed over the two halves of the microprocessor illustrated in FIGS. 3A–3C.

Figure 7A:
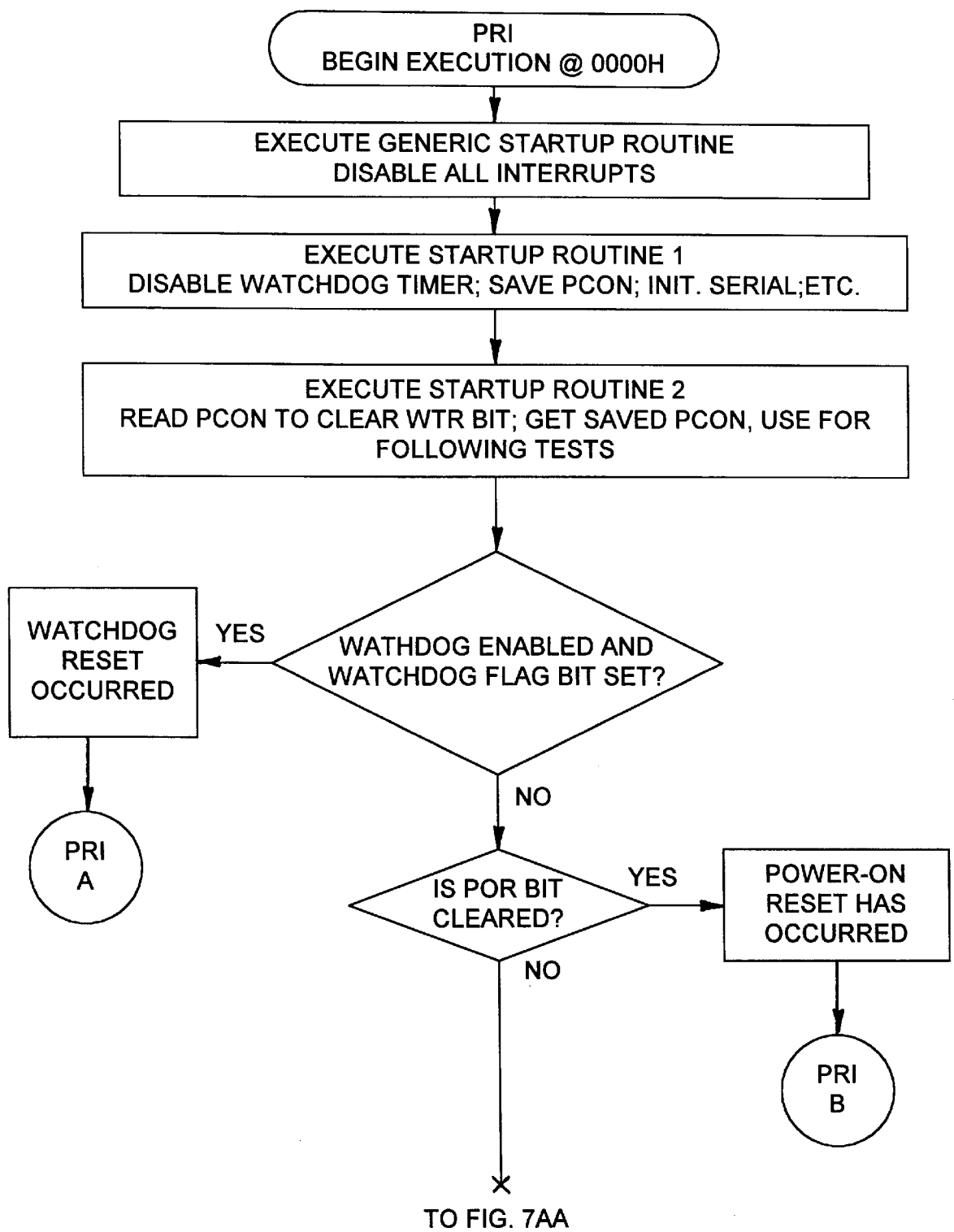
FIGS. 7A–7F illustrate the overall operation of a primary microprocessor to perform a direct lifetime measurement in the fluorometer circuit illustrated in FIGS. 3A–3C, according to the present invention.
Figure 7A:
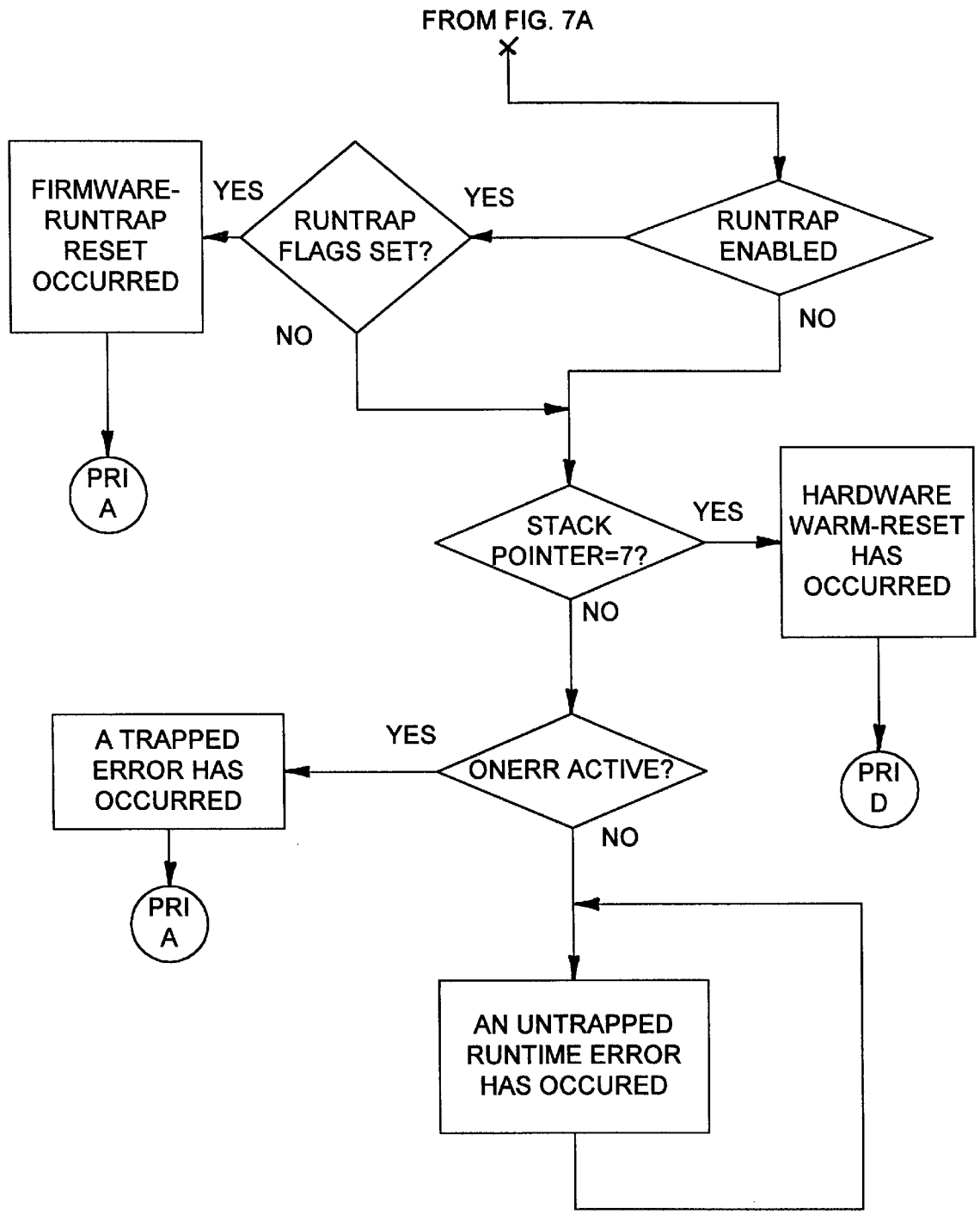
Figure 7B:
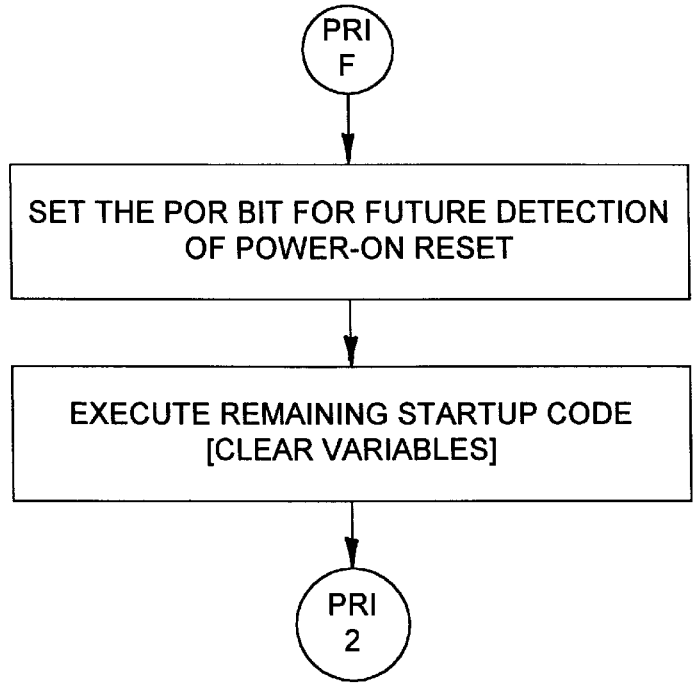
Figure 7C:
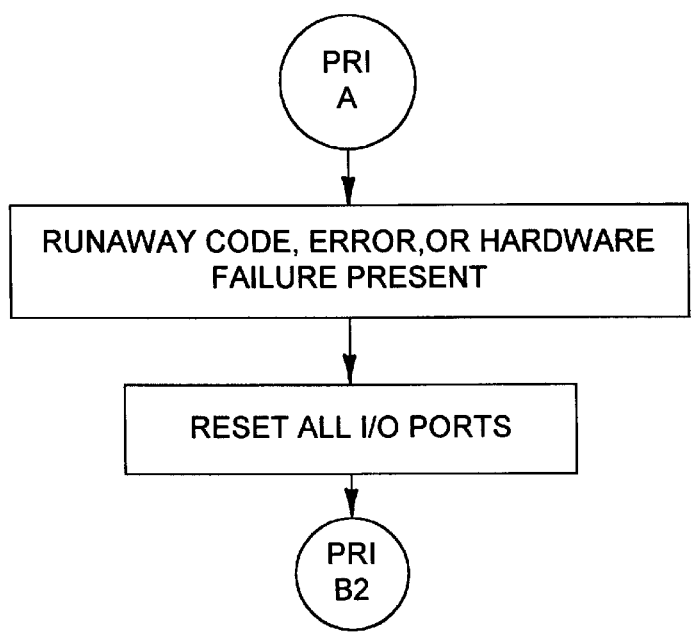
Figure 7D:
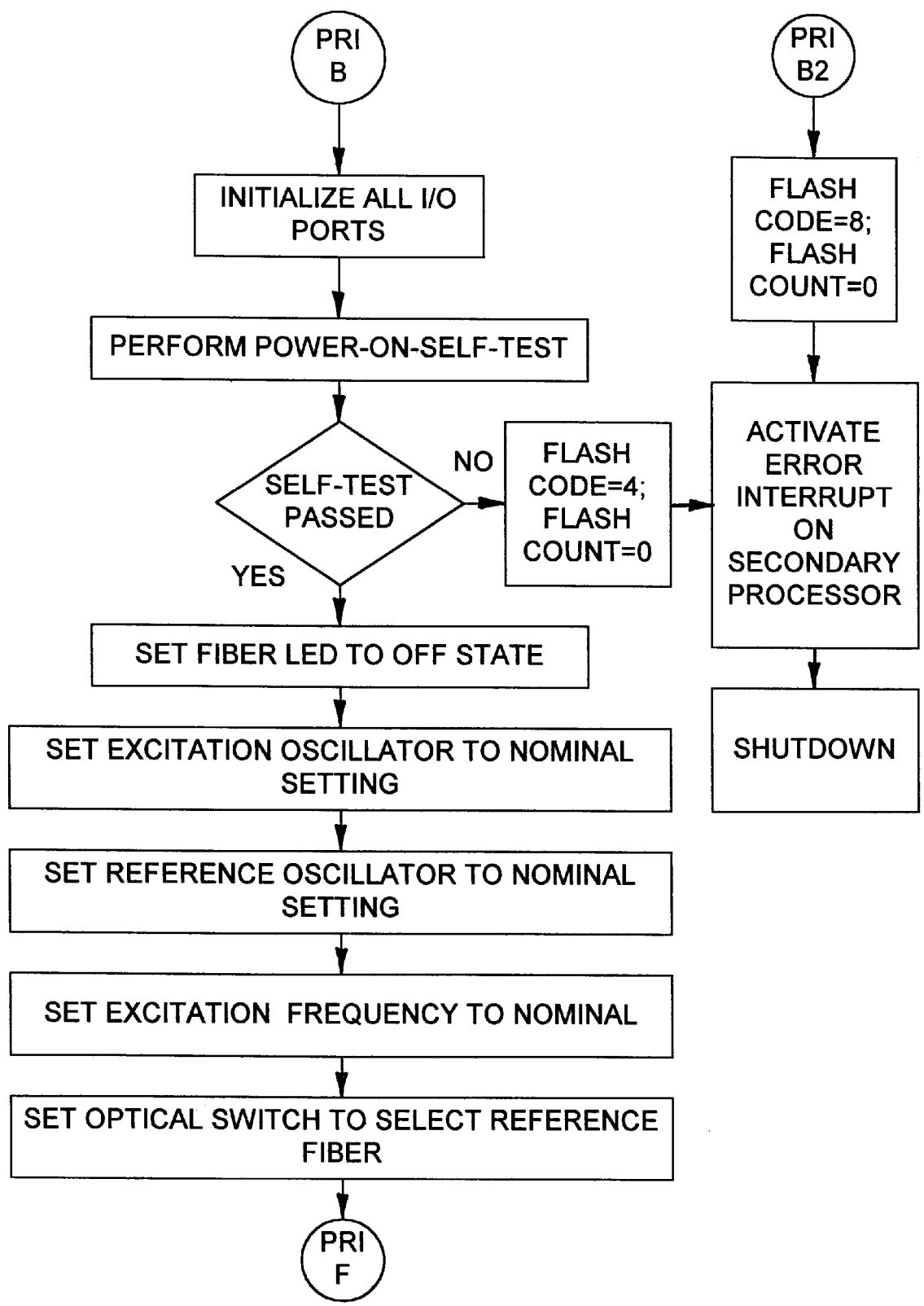

FIGS. 7A–7F illustrate the overall operation of the primary microprocessor, which oversees the measuring of time intervals. More specifically, FIGS. 7A and 7AA illustrates the steps which are necessary to initialize the microprocessor. The steps illustrated in FIGS. 7A and 7AA are generally applicable initialization steps which must always be performed, regardless whether the primary microprocessor is used for making fluorometric measurements. These steps relate to, for example, checking for power-on reset, setting error flags, and checking for errors during initialization. Similarly, FIGS. 7B–7D illustrate the steps taken when an error occurs during the initialization of the primary microprocessor. More information regarding these steps can be found in documentation applicable to the microprocessor used. The implementation of these steps is thus considered to be within the skill of a person skilled in the art, and will not be discussed further.

Figure 7E:
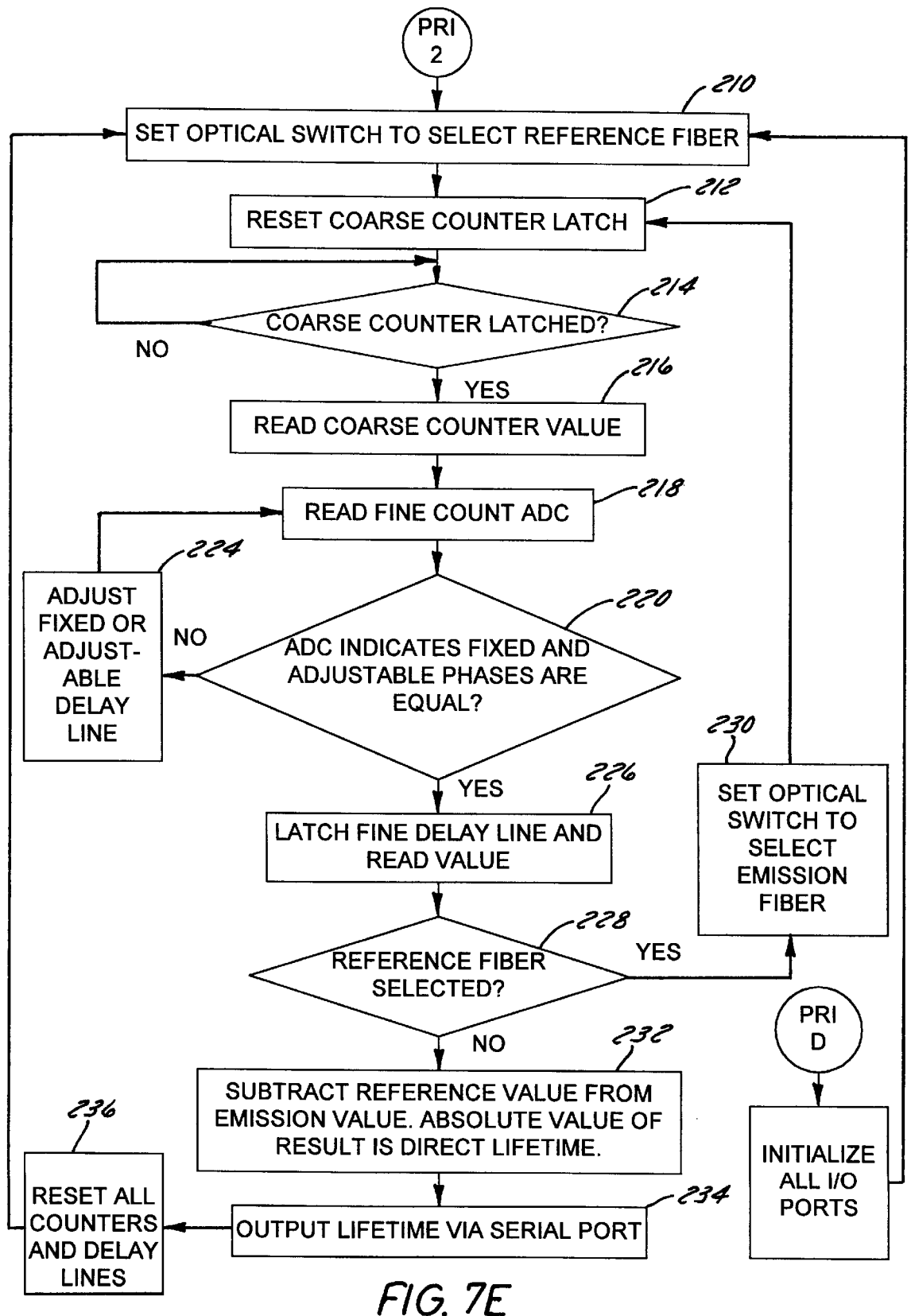

FIG. 7E illustrates the steps which pertain directly to performing fluorescence lifetime measurements. At step 210, the primary microprocessor sets the optical switch 82 to select the reference fiber. (The reference fiber is the optical fiber through which the excitation signal propagates.) Next, at step 212, the coarse counter 116 is latched and the coarse counter 116 begins counting. Then, at step 214, the primary microprocessor ascertains whether the coarse counter 116 has latched again. (The coarse counter 116 becomes latched again when the crossing is detected by the crossing detector 102.) The primary microprocessor repeats step 214 until it detects that the coarse counter 116 has latched.

Once the coarse counter 116 latches, the primary microprocessor reads the coarse counter 116 time value (i.e., the output bits of the coarse counter 116). The primary microprocessor then also reads the analog-digital converter 102 at step 218 and, based on the information provided by the analog-digital converter, determines whether the fixed and adjustable phases are equal (i.e., whether the fixed and adjustable delays terminate at the same instant) at step 220.

If the fixed and adjustable delays do not terminate at the same time instant, then either the fixed delay or adjustable delay is adjusted at step 224, and steps 218–220 are repeated. Initially, the fixed delay may be too long or too short, such that no amount of adjustment of the adjustable delay will cause the two delays to terminate at the same time instant. Thus, the fixed delay is adjusted so as to be brought "within range" of the adjustable delay. Thereafter, the adjustable delay is adjusted until the two delays terminate at the same time instant and the error signal is driven to a steady state zero value.

Once it has been determined that the fixed and adjustable delay lines terminate at the same instant, then the up/down counter 136 is latched and the primary microprocessor reads the output bits of the up/down counter 136 at step 226. The timing information ($T_{TOTAL}$ as defined above, hereinafter $T_{TOT-REF}$) is stored for the reference signal. After the primary microprocessor determines at step 228 that it has just made a measurement for the reference (excitation wavelength) signal, it sets the optical switch 82 to select the emission fiber at step 230. The process is then repeated for the emission signal to determine timing information (also $T_{TOTAL}$ as defined above, hereinafter $T_{TOT-EM}$) for the emission signal. The direct fluorescence lifetime is then calculated at step 232 (the direct fluorescence lifetime is equal to the absolute value of the difference between values $T_{REF-TOT}$ and $T_{EM-TOT}$), and is then output via serial port at step 234. All the counters and delays are then reset at step 236, and the entire process may be performed again.

Figure 7F:
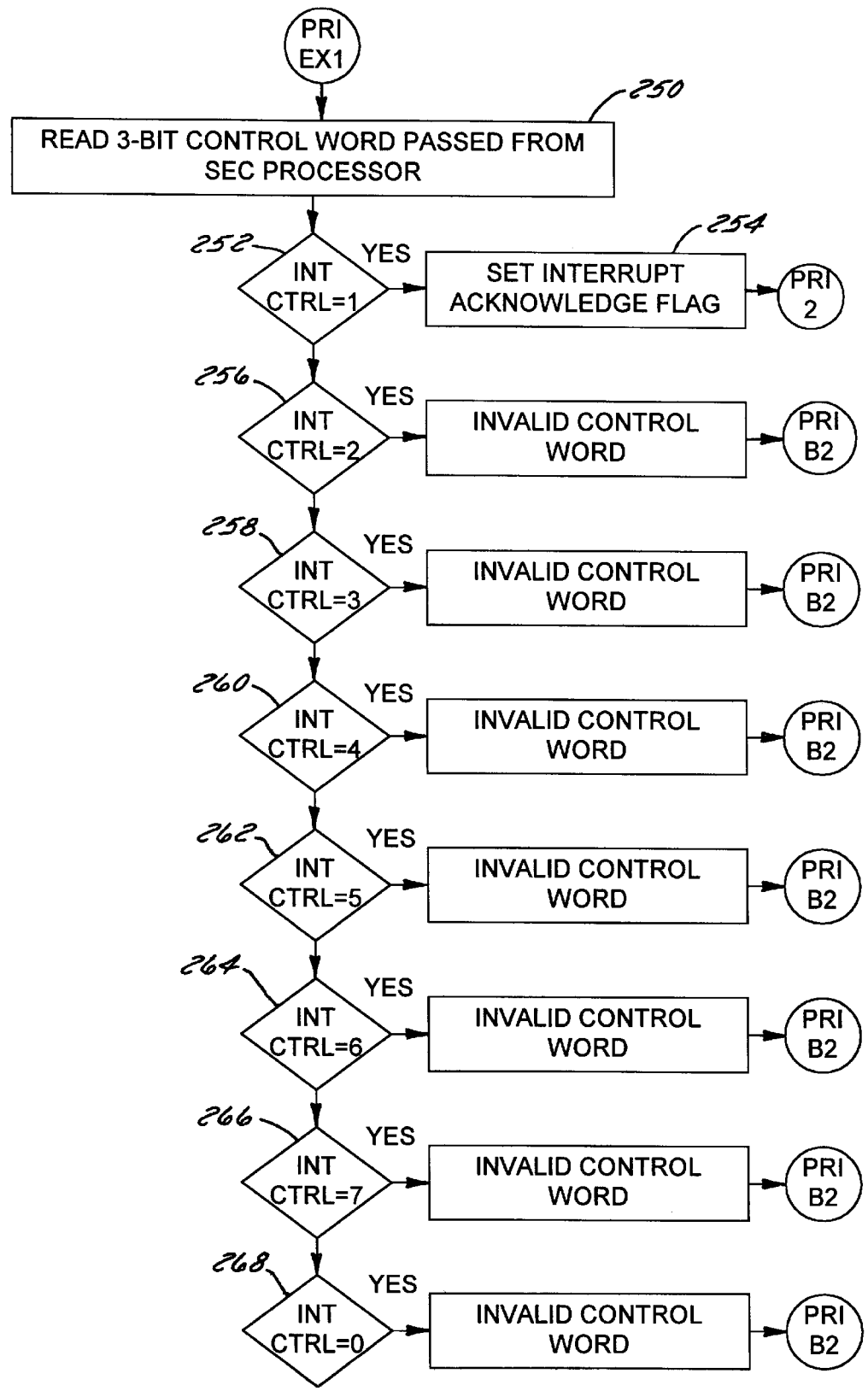

FIG. 7F illustrates the sequence of events which occurs when the primary microprocessor receives a primary external interrupt signal from the secondary microprocessor. The primary external interrupt is an interrupt input of the primary microprocessor and provides a way for the secondary microprocessor to send a message to the primary microprocessor. When the primary external interrupt signal is received, the primary microprocessor reads a three bit interrupt control word (Int Ctrl) passed from the secondary microprocessor at step 250. At step 252, the primary microprocessor determines whether Int Ctrl=1. If Int Ctrl=1, then the message is interpreted to mean that the secondary microprocessor is acknowledging an interrupt request from the primary microprocessor (discussed further below in conjunction with FIG. 8F). If Int Ctrl is not equal to one, then one of steps 256–268 is passed, the message is considered invalid, and the primary microprocessor executes a portion of the error handling routine as illustrated in FIG. 7C.

FIGS. 8A–8F illustrate the overall operation of the secondary microprocessor. The secondary processor is used for interfacing with the analog circuitry, and specifically for controlling the photomultiplier tube 26 and the crossing detector 102. FIGS. 8A–8D correspond to FIGS. 7A–7D, and therefore need not be discussed further.

Figure 8A:
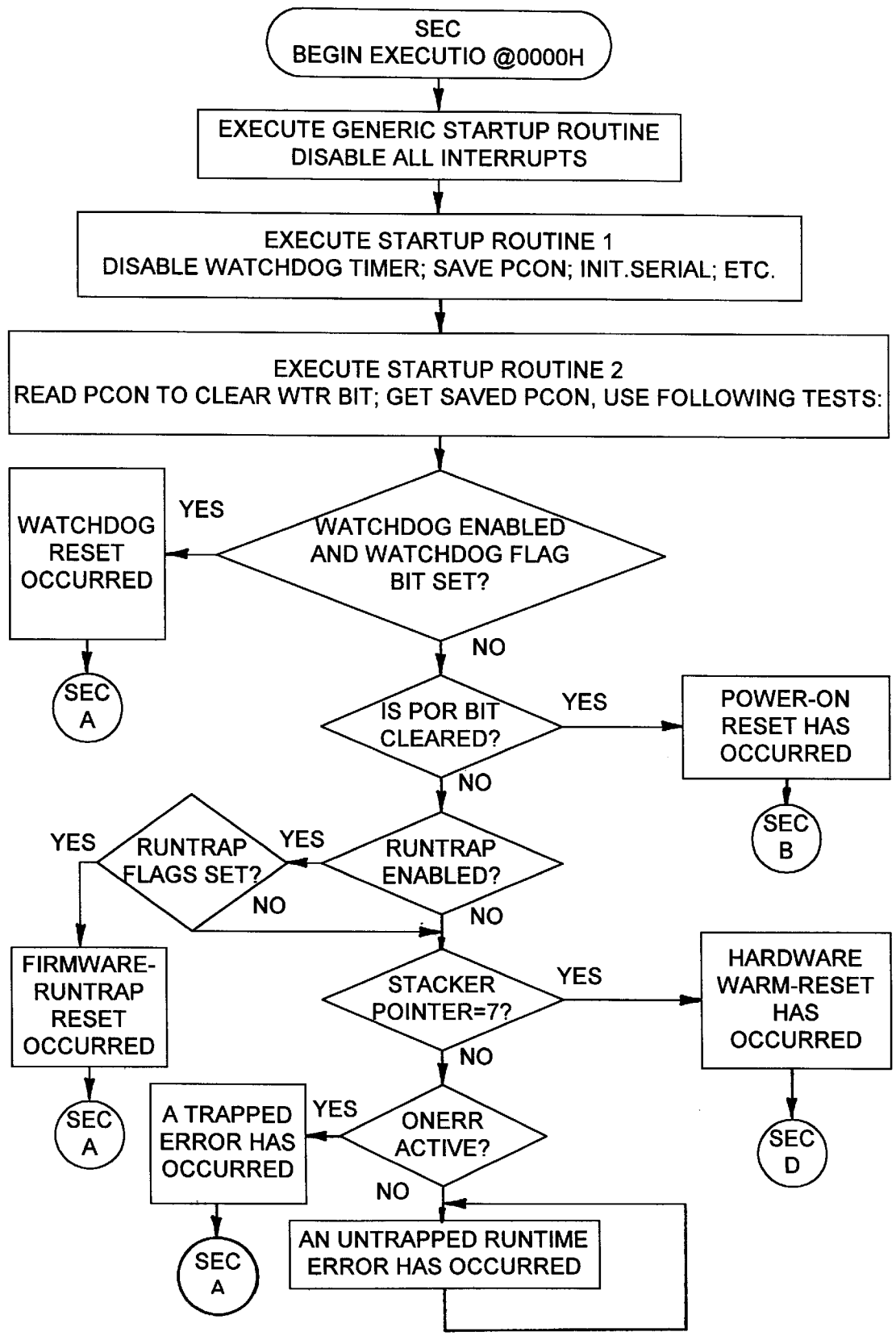
FIGS. 8A–8F illustrate the overall operation of a secondary microprocessor to perform a direct lifetime measurement in the fluorometer circuit illustrated in FIGS. 3A–3C, according to the present invention.
Figure 8B:
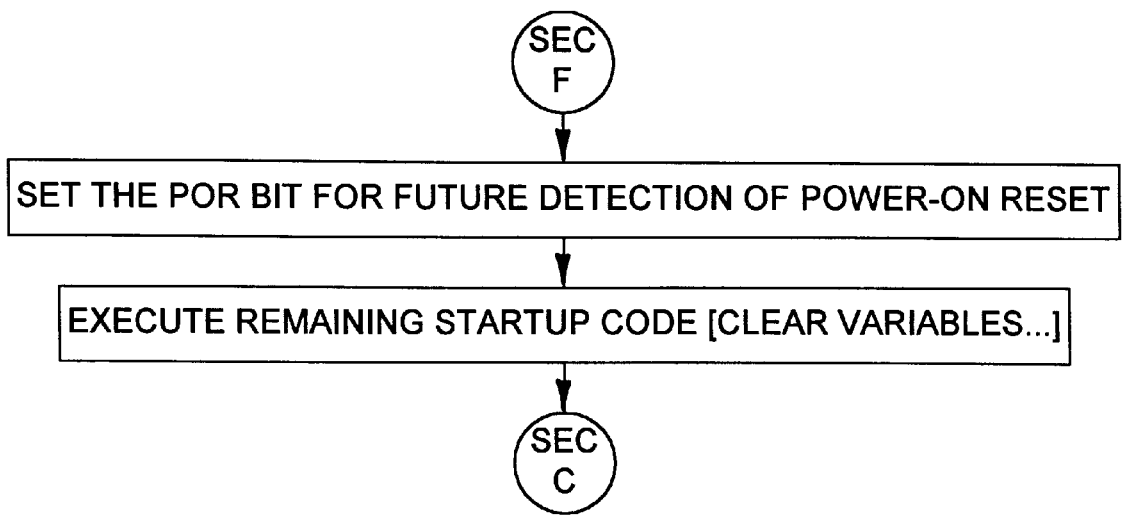
Figure 8D:
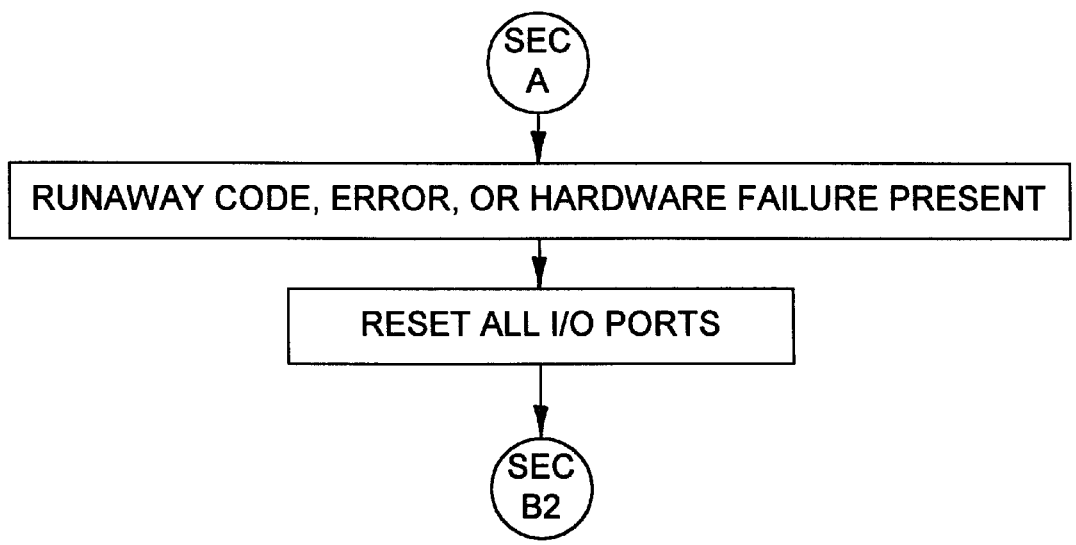
Figure 8C:
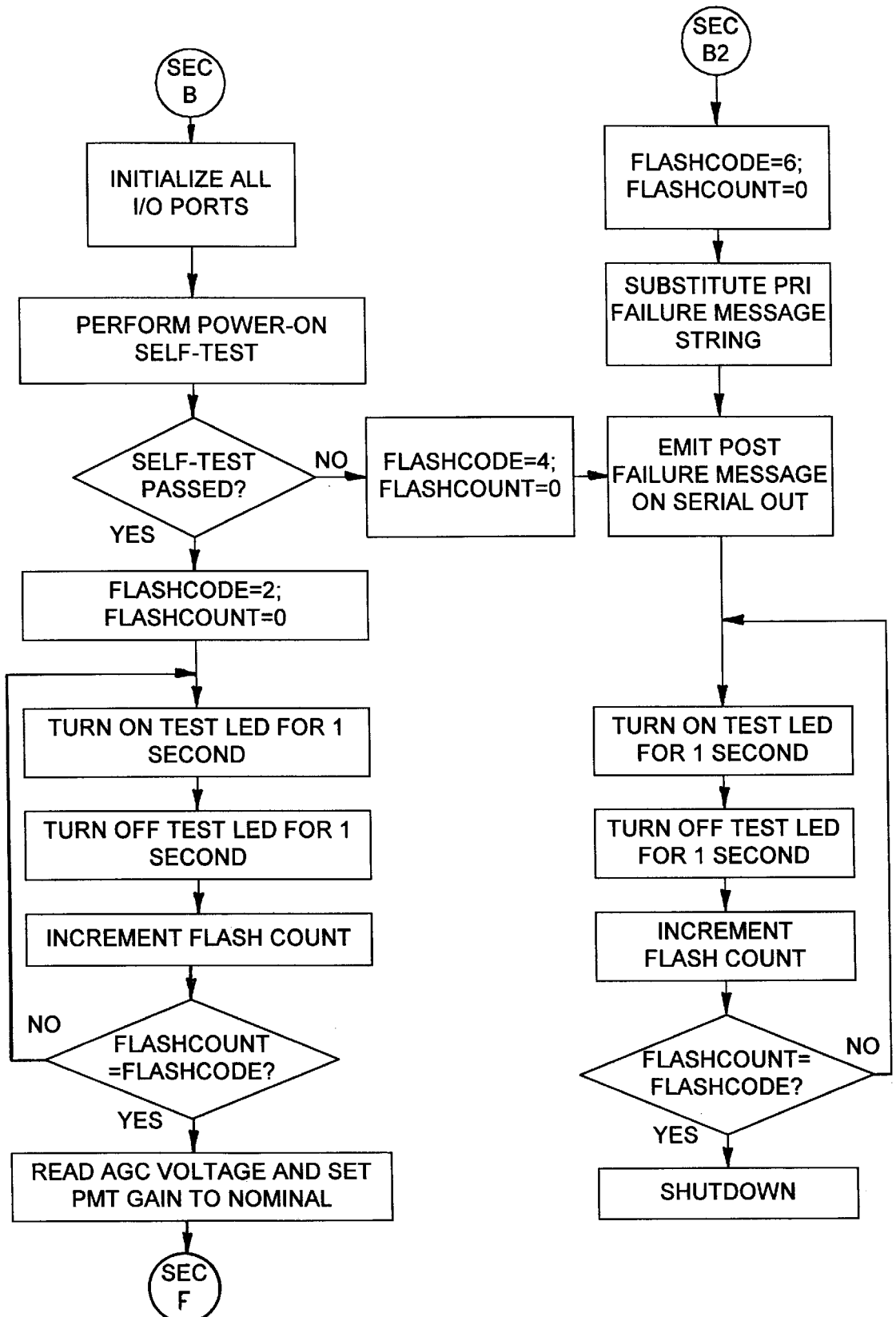
Figure 8E:
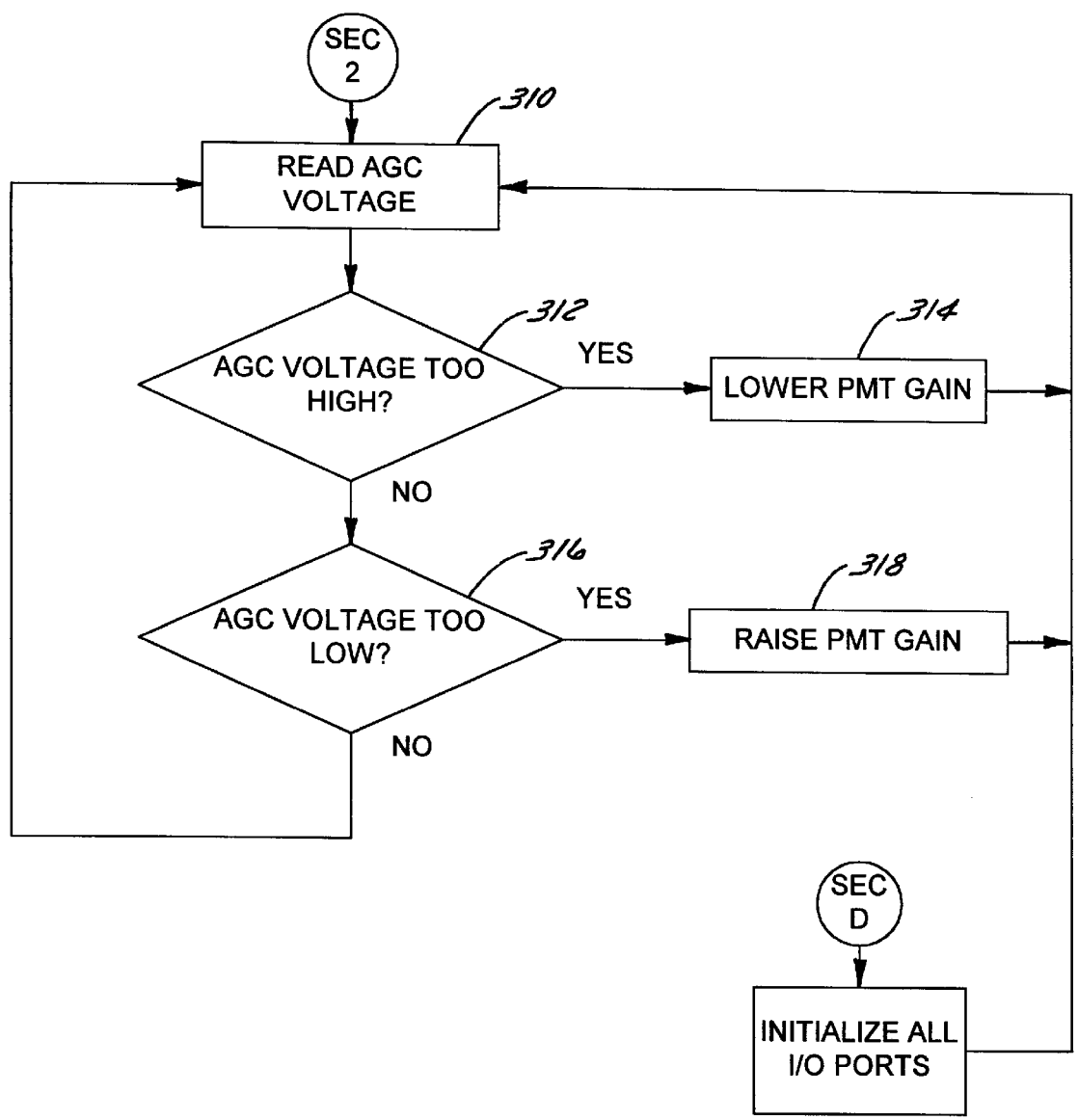

FIG. 8E illustrates the steps which pertain to setting the gain of the photomultiplier tube 26. At step 310, the voltage of the automatic gain control is read from the analog-digital converter 104. At step 312, it is determined whether the AGC voltage is too high. If the AGC voltage is too high, then the gain of the photomultiplier tube is lowered at step 314, and the process returns to step 310 and takes another AGC voltage reading.

If the AGC voltage is not too high at step 312, then at step 316 it is determined whether the AGC voltage is too low. If the AGC voltage is too low, then the gain of the photomultiplier tube is increased at step 318, and the process returns to step 310 and takes another AGC voltage reading. If the AGC voltage is neither too high nor too low, then the process simply returns to step 310 and takes another AGC voltage reading.

Figure 8F:
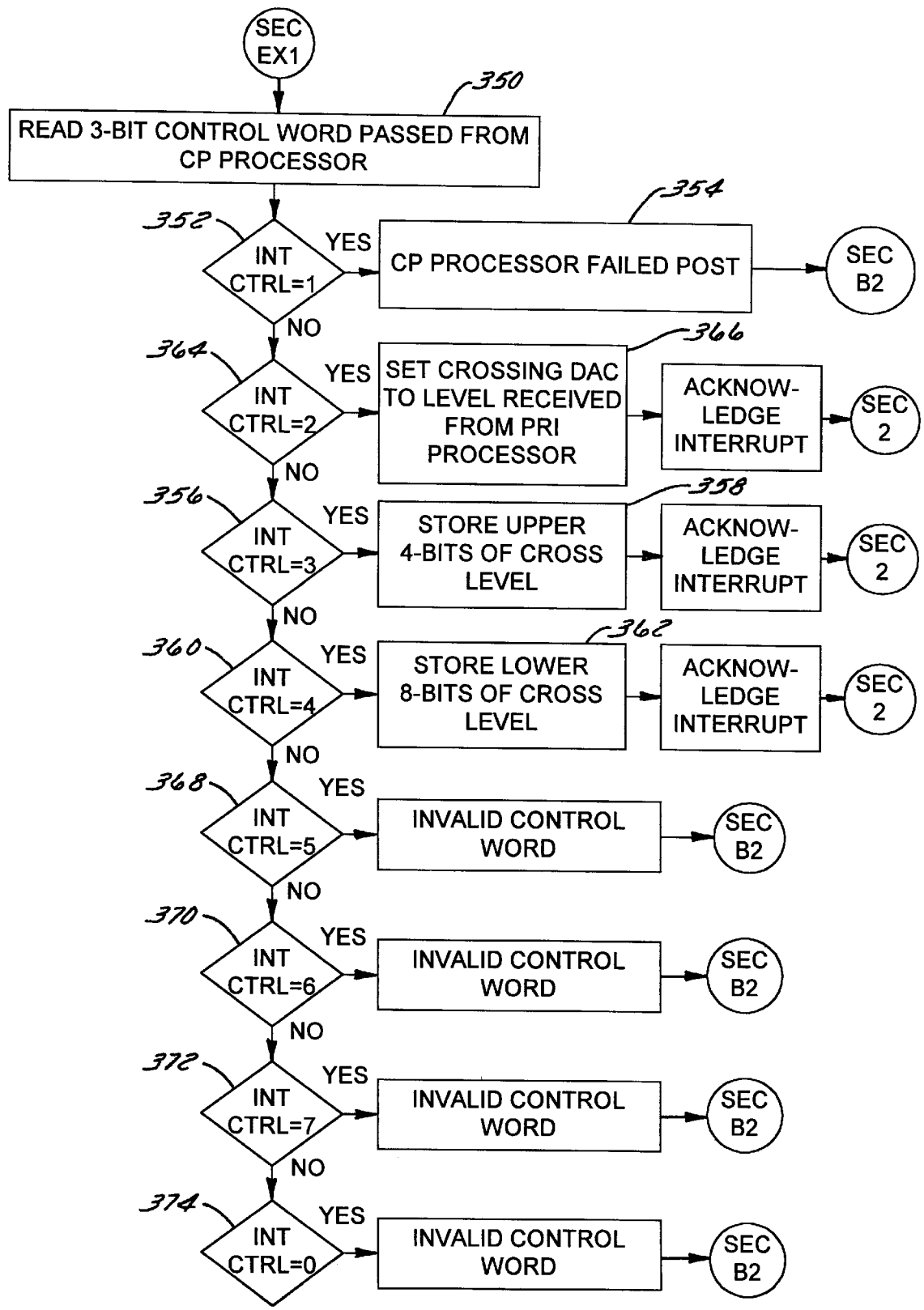

FIG. 8F illustrates the sequence of events which occurs when the secondary microprocessor receives a secondary external interrupt signal from the primary microprocessor. The secondary external interrupt is an interrupt input of the secondary microprocessor and provides a way for the primary microprocessor to send a message to the secondary microprocessor. When the secondary external interrupt signal is received, the primary microprocessor reads a three bit interrupt control word (Int Ctrl) passed from the secondary microprocessor at step 350.

At step 352, the primary microprocessor determines whether Int Ctrl=1. If Int Ctrl=1, then the message is interpreted to mean that the primary processor has failed its power-on self-test at step 354. Thus, if the primary processor fails its self-test, then the secondary processor executes the steps illustrated in FIG. 8C to notify the user that an error has occurred.

The purpose of steps 356–366 is to provide a way for the primary microprocessor to communicate a new desired level of the programmable crossing detector 102 to the secondary microprocessor, so that the secondary microprocessor can set the crossing detector 102 to the new desired level. At step 356, the secondary microprocessor determines whether Int Ctrl=3. If Int Ctrl=3, then the message is interpreted as containing the upper four bits of the new desired level at step 358. Similarly, at step 360, the secondary microprocessor determines whether Int Ctrl=4 and, if Int Ctrl=3, then the message is interpreted as containing the lower eight bits of the new desired level at step 362.

At step 364, the secondary microprocessor determines whether Int Ctrl=2. If Int Ctrl=2, then the message is interpreted as an instruction to set the crossing level in the digital-analog converter 104 to the level received from the primary microprocessor in steps 356–362.

If Int Ctrl>4, then one of steps 368–374 is passed, the message is considered to be invalid, and the secondary microprocessor executes a portion of the error handling routine as illustrated in FIG. 8C.

Figure 9A:
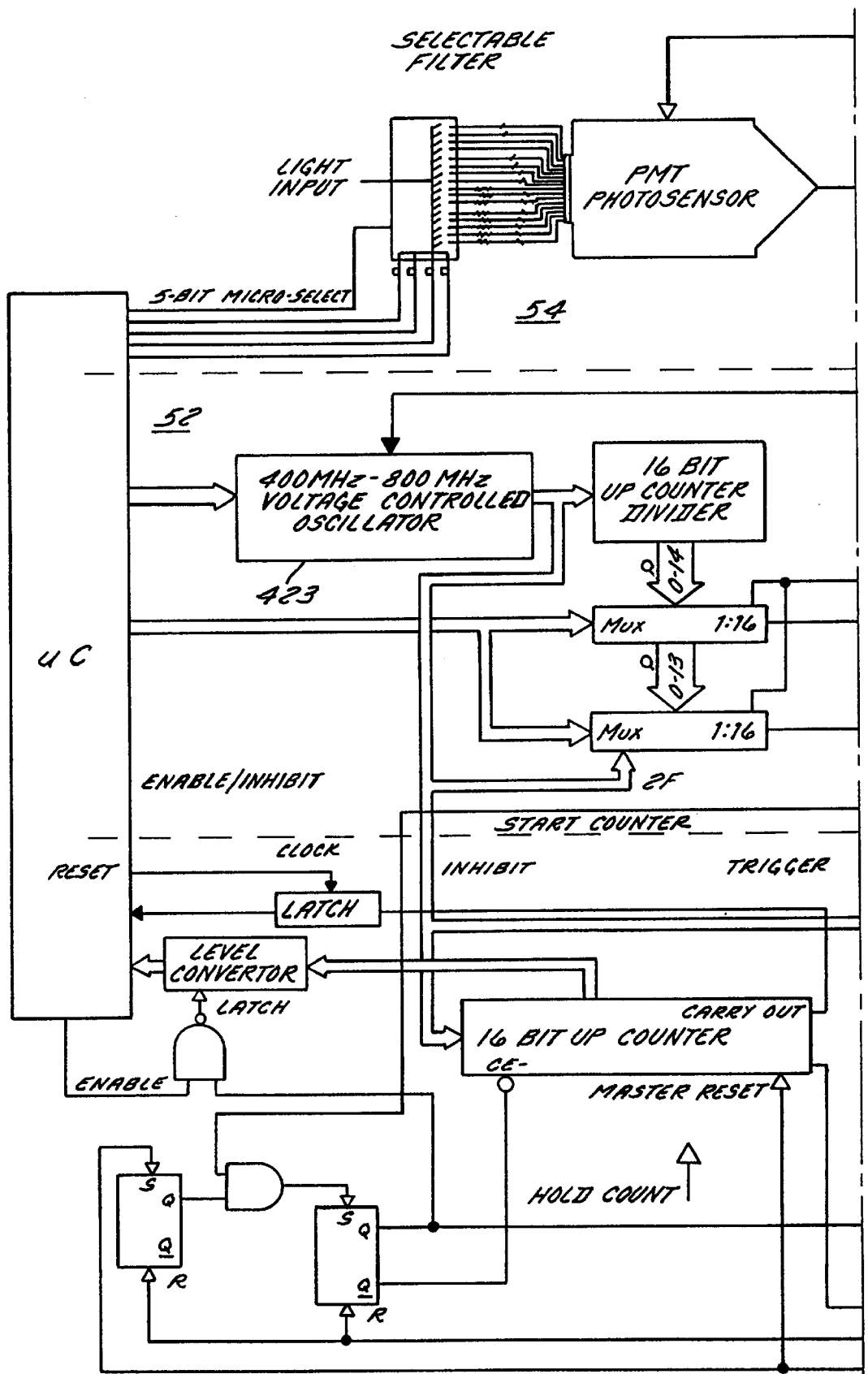
FIGS. 9A–9C illustrates an alternative embodiment of the fluorometer circuit illustrated in FIGS. 3A–3C, according to the present invention.
Figure 9B:
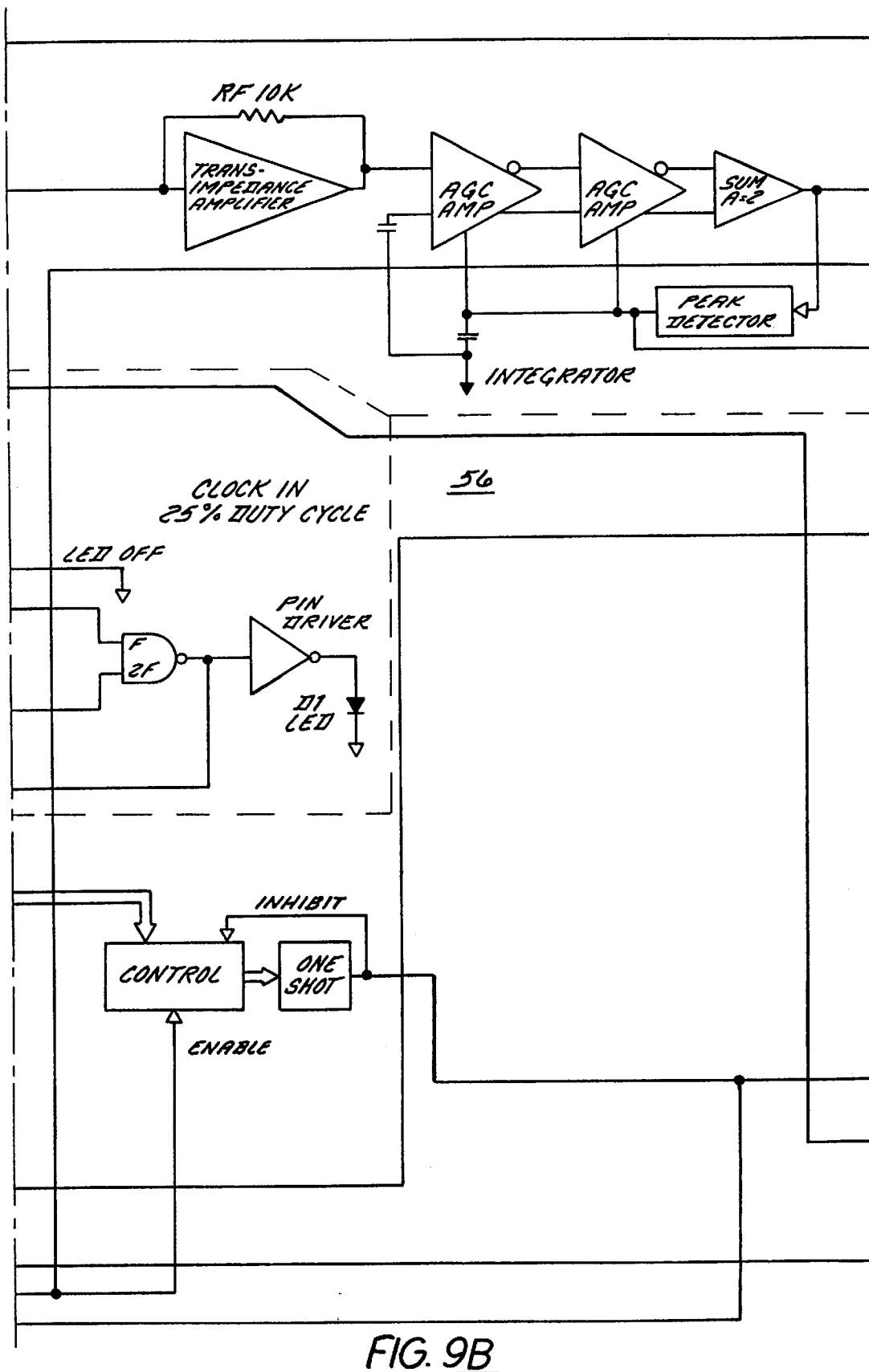
Figure 9C:
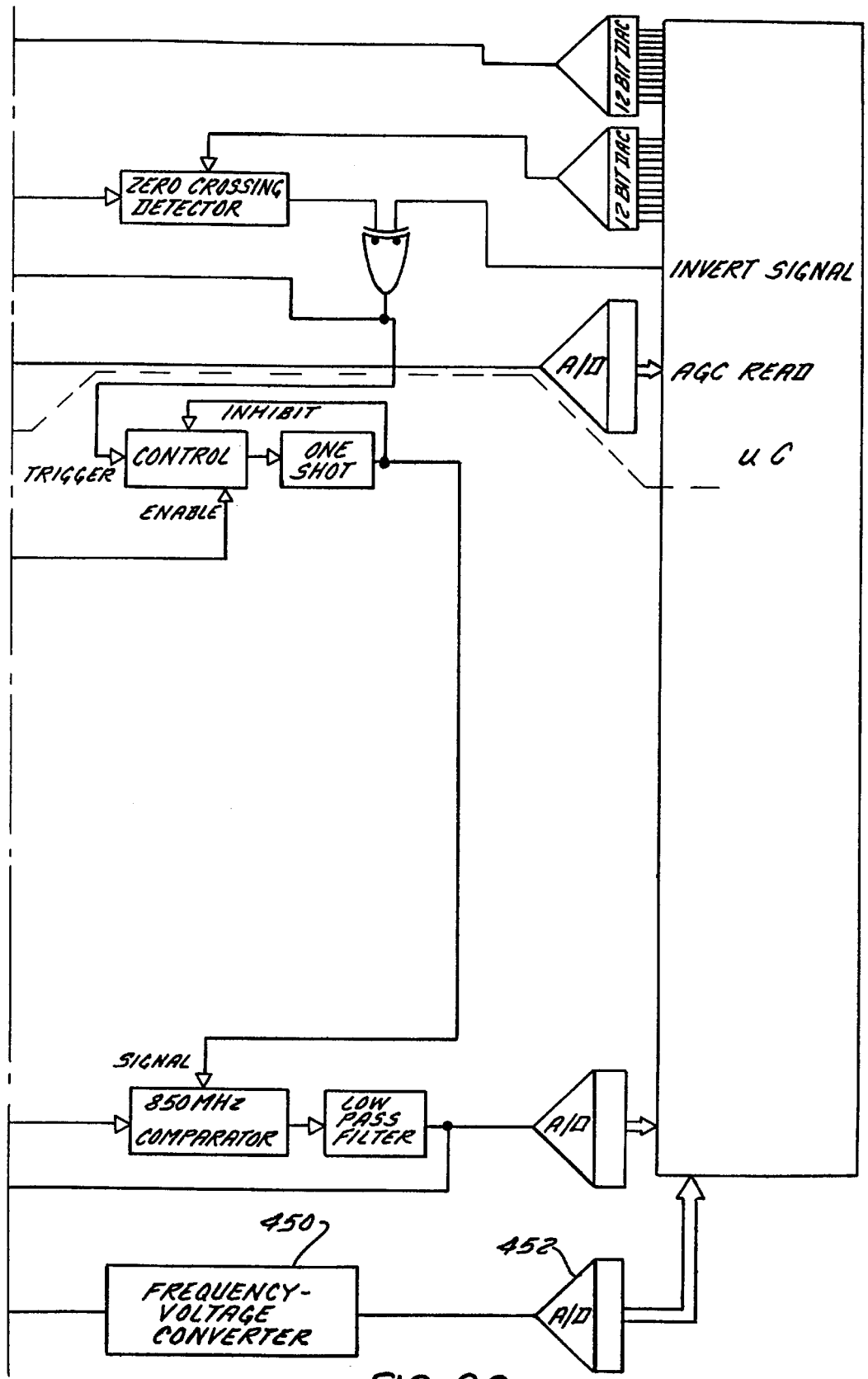

Referring now to FIGS. 9A–9C, a schematic circuit diagram of an alternative fluorometer circuit according to the present invention is illustrated. The alternative fluorometer circuit is the same as the fluorometer circuit illustrated in FIGS. 3A–3C, except that the delays 124 and 134 have been eliminated and the programmable oscillator 23 has been replaced with a voltage controlled oscillator 423.

As will be recalled, in the fluorometer circuit illustrated in FIGS. 3A–3C, the problem addressed by the delays 124 and 134 is that the instant at which the last state change of the coarse counter 116 occurs is not the same as the instant at which the crossing is detected by the crossing detector 102. The delays 124 and 134 address this problem by measuring the time interval between the difference in time between these two instances.

In the fluorometer circuit illustrated in FIGS. 9A–9C, a different approach is taken. Specifically, the frequency of the voltage controlled oscillator 423 is iteratively adjusted until a state change of the coarse counter 116 coincides with the crossing detection. When this occurs, the microprocessor 58 reads the output bits of the coarse counter 116, and uses a voltage frequency converter 450 coupled to an analog-digital converter 452 to determine the precise frequency of the voltage controlled oscillator. Using this information, the microprocessor 58 is able to calculate the bit weight of each bit of the coarse counter 116, and is able to calculate the total elapsed time between the instant at which the LED 25 was initially illuminated and the instant at which the crossing occurred.

As well, other circuits could be used in conjunction with the fluorometers illustrated in FIGS. 1A–1D and FIG. 2. For example, the fluorometer illustrated in FIG. 2 could be a phase fluorometer which operates based on heterodyning principles.

A number of additional advantageous features of the fluorometer according to the present invention should thus be noted. First, the fluorometer 20 uses the excitation signal returned from the system under study as a reference signal to facilitate calibration and nullify distortion. Once the excitation signal exits the optical output 21, there is a certain amount of delay associated with the time required for the excitation and emission signals to propagate through the optical fibers. The propagation delay is a function of the length of the optical fibers. There is also a certain amount of delay inherent in the electronic circuitry used to detect and process the optical signals. The use of the excitation signal as a reference signal provides a convenient way to account for this delay when the emission signal is processed. Further, since both the excitation signal and the emission signal are propagated and electrically processed under very similar conditions (e.g., similar temperature conditions, similar fibers, similar fiber lengths, etc.), the use of the excitation signal as a reference signal provides a convenient way to nullify any distortions which occur during the propagation of the emission signal. Thus, by subtracting the reference signal from the emission signal, the fluorometer 20 is able to calibrate itself and eliminate numerous distortions.

Second, the fluorometer uses automatic gain control circuitry in the detection subcircuit 52 to greatly simplify signal processing in the signal processing subcircuit 54. The automatic gain control circuitry causes the peaks and the slopes of pulses of the emission and excitation signals to be held constant. Thus, regardless of amplitude variations caused by testing conditions, the automatic gain control circuitry enables the pulses of the emission and excitation signals to have a constant shape when viewed by the signal processing subcircuit 54.

Third, the fluorometer 20 uses a programmable crossing detector 102 which enables pulse profiling. By varying the crossing level which the programmable detector 102 detects, and by looking at both the rising and falling pulse edges, the pulses of the excitation and the emission signals may be profiled. Also, the fluorometer 20 may be used not only for direct fluorescence lifetime measurements, but also for phase fluorometry. This is especially advantageous because phase fluorometry, as compared to fluorometry based on direct fluorescence lifetime measurements, is more suitable for studying complex multi-exponential decays.

Many changes and modifications may be made to the present invention without departing from the spirit thereof. The scope of these and other changes will become apparent from the appended claims.

We claim:

1. A fluorescence spectroscopy method comprising the steps of:
   (A) venerating an excitation signal at a fluorometer;
   (B) transmitting said excitation signal to a system under study which, in response, generates an emission signal, and then transmitting said excitation signal and said emission signal from said system under study to said fluorometer; and
   (C) detecting said excitation signal and said emission signal with said fluorometer, said detected excitation signal and said detected emission signal both being received from said system under study;
   (D) using said detected excitation signal as a reference signal to calibrate said fluorometer and to nullify distortion errors in said detected emission signal; and
   (E) processing said emission signal to produce timing information, said processing step including the steps of
      (1) detecting when said emission signal crosses a predetermined level;
      (2) initiating a first delay when said emission signal crosses said predetermined level;
      (3) detecting when a coarse counter changes state;
      (4) initiating a second delay when said coarse counter changes state;
      (5) causing said first delay and said second delay to terminate approximately simultaneously by adjusting the duration of at least one of said first and second delays;
      (6) obtaining said timing information, including
         (a) reading the value of said coarse counter to obtain relatively low precision timing information,
         (b) determining the duration of said first and second delays to obtain relatively high precision timing information, and
         (c) combining said high precision timing information with said low precision timing information.

2. A fluorescence spectroscopy method comprising the steps of:
   (A) generating an excitation signal at a fluorometer;
   (B) transmitting said excitation signal to a system under study which, in response, generates an emission signal, and then transmitting said excitation signal and said emission signal from said system under study to said fluorometer; and
   (C) detecting said emission signal with said fluorometer, said detected emission signal being received from said system under study; and
   (D) processing said emission signal to produce timing information, said processing step including the steps of
      (1) detecting when said emission signal crosses a predetermined level;
      (2) detecting when a counter changes state;
      (3) generating a difference signal based on the difference in time between when said emission signal crosses said predetermined level and when said counter changes state;
      (4) iteratively adjusting an adjustable oscillator based on said difference signal, said adjustable oscillator driving state changes of said counter, and said adjustable oscillator being iteratively adjusted until said emission signal crosses said predetermined level at approximately the same time as when said counter changes state; and
      (5) obtaining said timing information by determining the frequency of said adjustable oscillator and by determining the value of said counter at least when said iteratively adjusting step is complete.

3. A fluorescence spectroscopy method comprising the steps of:
   (A) generating an excitation signal at a fluorometer;
   (B) transmitting said excitation signal to a system under study which, in response, generates an emission signal, and then transmitting said excitation signal and said emission signal from said system under study to said fluorometer; and
   (C) detecting said emission signal with said fluorometer, said detected emission signal being received from said system under study; and
   (D) processing said emission signal to produce timing information, said processing step including the steps of
      (1) detecting when said emission signal crosses a predetermined level;
      (2) obtaining said timing information based on when said emission signal crosses said predetermined level; and (3) adjusting said predetermined level and repeating said detecting and obtaining steps, said adjusting and repeating steps being performed a plurality of times so as to obtain a plurality of data points which profile the exponential decay of said emission signal.

4. The method according to claim 3, further comprising the steps of providing said fluorometer, said fluorometer comprising (i) an oscillator; (ii) a excitation source which is coupled to said oscillator and which generates said excitation signal; (iii) a wavelength selector which receives said emission signal from said system under study and which filters out components of light received from said system under study which are not components of said emission signal; and (iv) a detector which is coupled to said wavelength selector and which detects said emission signal;

wherein said excitation source is provided as a modular excitation source which is removable and replaceable with a plurality of additional excitation sources such that said fluorometer is operable to generate a plurality of additional excitation signals having different excitation wavelengths, depending on the excitation source used;

wherein said excitation source and said plurality of additional excitation sources are each substantially monochromatic, such that an operating range of said fluorometer at a given instant is limited to a specific narrow range of wavelengths corresponding to the excitation source used.

5. The method according to claim 4 wherein, during said providing step, said fluorometer either (i) is packaged on an expansion card which is removably insertable into an expansion slot of a personal computer, or (ii) is packaged as a stand-alone peripheral for a personal computer and has a size which is not substantially larger than that of said personal computer.

6. The method according to claim 5, wherein the generating, detecting and processing steps are all performed using exclusively solid-state components.

7. A fluorescence spectroscopy method comprising the steps of:

(A) generating an excitation signal at a fluorometer;

(B) transmitting said excitation signal to a system under study which, in response, generates an emission signal, and then transmitting said excitation signal and said emission signal from said system under study to said fluorometer; and (C) detecting said emission signal with said fluorometer, said detected emission signal being received from said system under study; and (D) providing said fluorometer with automatic gain control circuitry; and (E) holding pulse shapes of said emission signal substantially constant using said automatic gain control circuitry.

8. A fluorescence spectroscopy method comprising the steps of:

(A) generating an excitation signal at a fluorometer, said fluorometer either (i) being packaged on an expansion card which is removably insertable into an expansion slot of a personal computer, or (ii) being packaged as a stand-alone peripheral for a personal computer and has a size which is not substantially larger than that of said personal computer;

(B) transmitting said excitation signal to a system under study which, in response, generates an emission signal, and then transmitting said emission signal from said system under study to said fluorometer;

(C) detecting said emission signal with said fluorometer;

(D) processing said emission signal to produce timing information, said processing step including the steps of (1) detecting when said emission signal crosses a predetermined level;

(2) obtaining said timing information based on when said emission signal crosses said predetermined level; and (3) adjusting said predetermined level and repeating said detecting and obtaining steps, said adjusting and repeating step being performed a plurality of times so as to obtain a plurality of data points which profile the exponential decay of said emission signal.

9. The method according to claim 8, wherein said generating step is performed using a solid-state modular excitation source which is removable and replaceable with a plurality of additional excitation sources such that said fluorometer is operable to generate a plurality of additional excitation signals having different excitation wavelengths, depending on the excitation source used, and wherein said excitation source and said plurality of additional excitation sources are each substantially monochromatic, such that an operating range of said fluorometer at a given instant is limited to a specific narrow range of wavelengths corresponding to the excitation source used.

10. The method according to claim 9, wherein said transmitting step is performed using an optical interface which interfaces said fluorometer with said system under study, and wherein said optical interface is exclusively fiber optic-based.

11. The method according to claim 10, wherein the generating detecting and processing steps are all performed using exclusively solid-state components.

12. The method according to claim 11, further comprises the steps of detecting said excitation signal after said excitation signal has returned from said system under study; and using said detected excitation signal as a reference signal to calibrate said fluorometer and to nullify distortion errors in said detected emission signal.

13. A fluorometer comprising:

(A) a solid-state, modular, removable and replaceable excitation source, said excitation source being substantially monochromatic, and said excitation source generating an excitation signal which is provided to a system under study;

(B) a solid-state, modular, removable and replaceable wavelength selector, said wavelength selector receiving an emission signal generated by said system under study in response to said excitation signal and filtering out components of light received from said system under study which are not components of said emission signal;

(C) a detector, said detector being coupled to said wavelength selector, and said detector detecting said emission signal;

(D) a solid-state signal processor, said signal processor being coupled to said detector, and said signal processor processing said emission signal; and (E) an optical interface, including (1) a fiber optic output, said fiber optic output being coupled to said excitation source, (2) a first optical fiber, said first optical fiber being coupled to said fiber optic output and delivering said excitation signal to said system under study, (3) a fiber optic input, said fiber optic input being coupled to said detector, and (4) a second optical fiber, said second optical fiber being coupled to said fiber optic input and delivering said emission signal from said system under study to said fiber optic input, (F) a programmable crossing detector which enables said fluorometer to profile the exponential decay of said emission signal; and wherein said optical interface is the only optical interface between said fluorometer and said system under study through which fluorometric signals are communicated, and wherein said optical interface is exclusively fiber optic-based.

14. The fluorometer according to claim 13, wherein said detector detects both said emission signal and said excitation signal, said detected emission signal and said detected excitation signal both being received from said system under study;

wherein said fluorometer further comprises a signal processor which is coupled to said detector which processes said detected emission signal;

wherein said signal processor uses said detected excitation signal as a reference signal to calibrate said fluorometer and to nullify distortion errors in said detected emission signal.

15. A fluorometer comprising:

an excitation source for generating an excitation signal and transmitting said excitation signal to a system under study;

a wavelength selector for receiving an emission signal generated by said system under study in response to said excitation signal;

a detector coupled to said wavelength collector for detecting said emission signal;

a programmable crossing detector that enables the fluorometer to profile the exponential decay of said emission signal; and a signal processor coupled to said detector for receiving and processing said emission signal.

16. A fluorometer according to claim 15, further including an optical interface between the fluorometer and said system under study through which fluorometric signals are communicated, said optical interface being exclusively fiber optic based.

17. A fluorescence spectroscopy method comprising the steps of:

(A) generating an excitation signal at a fluorometer;

(B) transmitting said excitation signal to a system under study which, in response, generates an emission signal, and then transmitting said excitation signal and said emission signal from said system under study to said fluorometer; and (C) detecting said emission signal and said excitation signal with said fluorometer, said detected emission and said excitation signal being received from said system under study; and (D) using a crossing detector to determine a phase difference between said excitation signal and said emission signal.

18. A method according to claim 17, further comprising the steps of, (A) processing said emission signal and said excitation signal to produce timing information, said processing step including the steps of (1) detecting a crossing when said emission signal crosses a predetermined level;

(2) initiating first and second delays, one of said first and second delays being initiated when said emission signal crosses said predetermined level;

(3) causing said first delay and said second delay to terminate approximately simultaneously by adjusting the duration of at least one of said first and second delays; and (4) producing said timing information based on said adjusting step.

19. A method according to claim 18, further comprising the step of obtaining said timing information by determining a total elapsed time between said generation of said excitation signal and said detection of said crossing.

20. A method according to claim 17, further comprising the steps of, (A) processing said emission signal to produce timing information, said processing step including the steps of (1) determining a first instant in time at which a first event occurs, said first instant in time being determined by when said emission signal crosses a perdetermined level;

(2) determining a second instant in time at which a second event occurs, said second instant in time being adjustable; and (3) causing said first event and said second events to occur substantially simultaneously by adjusting when said second instant in time occurs.

21. A fluorescence spectroscopy method comprising the steps of:

(A) generating an excitation signal at a fluorometer;

(B) transmitting said excitation signal to a system under study which, in response, generates an emission signal, and then transmitting said excitation signal and said emission signal from said system under study to said fluorometer; and (C) processing said emission signal to produce timing information, said processing step including the steps of (1) detecting when said emission signal crosses a predetermined level;

(2) obtaining said timing information based on when said emission signal crosses said predetermined level; and (3) adjusting said predetermined level and repeating said detecting and obtaining steps, said adjusting and repeating steps being performed a plurality of times so as to obtain a plurality of data points which profile the exponential decay of said emission signal.

* * * * *